(12) United States Patent
Miyamoto et al.

(10) Patent No.: US 8,894,668 B2
(45) Date of Patent: Nov. 25, 2014

(54) SURGICAL INSTRUMENT

(75) Inventors: Manabu Miyamoto, Tokyo (JP); Shuhei Iizuka, Shizuoka (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 12/273,739

(22) Filed: Nov. 19, 2008

(65) Prior Publication Data

US 2009/0076527 A1 Mar. 19, 2009

Related U.S. Application Data

(60) Division of application No. 11/403,037, filed on Apr. 12, 2006, now abandoned, which is a continuation of application No. PCT/JP2005/000848, filed on May 10, 2005.

(30) Foreign Application Priority Data

| May 11, 2004 | (JP) | 2004-141513 |
|---|---|---|
| Feb. 28, 2005 | (JP) | 2005-054020 |

(51) Int. Cl.
| A61B 17/04 | (2006.01) |
|---|---|
| A61B 17/29 | (2006.01) |
| A61B 17/062 | (2006.01) |
| A61B 17/11 | (2006.01) |
| A61B 17/28 | (2006.01) |

(52) U.S. Cl.
CPC ............. *A61B 17/29* (2013.01); *A61B 17/062* (2013.01); *A61B 17/11* (2013.01); *A61B 17/0493* (2013.01); *A61B 2017/1107* (2013.01); *A61B 2017/1135* (2013.01); *A61B 2017/2825* (2013.01)
USPC ............ 606/147; 606/148; 606/205; 606/206

(58) Field of Classification Search
CPC ............. A61B 17/062; A61B 17/0483; A61B 17/06061; A61B 17/28
USPC ......... 606/139, 144, 147, 148, 158, 205, 206, 606/207
See application file for complete search history.

(56) References Cited

U.S. PATENT DOCUMENTS

| 3,168,097 A | * | 2/1965 | Dormia | 606/147 |
| 3,878,848 A | | 4/1975 | Hiebert | 128/334 |

(Continued)

FOREIGN PATENT DOCUMENTS

| DE | 759 986 | 3/1953 |
| DE | 42 33 405 | 4/1994 |

(Continued)

OTHER PUBLICATIONS

International Search Report PCT/JP2005/008484 dated Aug. 3, 2005.

(Continued)

*Primary Examiner* — Julian W Woo
*Assistant Examiner* — Jing Ou
(74) *Attorney, Agent, or Firm* — Ostrolenk Faber LLP

(57) ABSTRACT

A surgical instrument for holding a suturing needle comprises an operating section, an insert section having an insert-section distal end extension at a distal end of an insert section body, a clamping portion, a rotatable holder portion, a receiving member having a first contact surface, and a transmitting member having a second contact surface. The insert section body has an inner bore along a first axis in a longitudinal direction. The insert-section distal end extension has a rotation-allowing groove on an inner peripheral surface of an inner bore provided along a second axis at a predetermined angle with respect to the first axis. The rotatable holder portion is allowed to be passively rotatable about the second axis under an external force applied to the suturing needle when a gap is formed between the transmitting member and the receiving member.

4 Claims, 27 Drawing Sheets

(56) References Cited

U.S. PATENT DOCUMENTS

| | | | | |
|---|---|---|---|---|
| 4,106,508 | A | * | 8/1978 | Berlin .......................... 606/158 |
| 4,621,640 | A | * | 11/1986 | Mulhollan et al. ............ 606/144 |
| 5,254,130 | A | * | 10/1993 | Poncet et al. ................. 606/206 |
| 5,300,082 | A | * | 4/1994 | Sharpe et al. ................. 606/147 |
| 5,342,375 | A | | 8/1994 | Lemole ......................... 606/148 |
| 5,417,701 | A | | 5/1995 | Holmes ......................... 606/148 |
| 5,490,858 | A | | 2/1996 | Shuter ........................... 606/148 |
| 5,507,796 | A | | 4/1996 | Hasson |
| 5,556,402 | A | | 9/1996 | Xu ................................. 606/147 |
| 5,810,877 | A | | 9/1998 | Roth et al. ..................... 606/205 |
| 5,879,371 | A | | 3/1999 | Gardiner et al. .............. 606/224 |
| 5,904,690 | A | | 5/1999 | Middleman et al. .......... 606/113 |
| 5,951,575 | A | * | 9/1999 | Bolduc et al. ................. 606/144 |
| 5,993,466 | A | * | 11/1999 | Yoon .............................. 606/147 |
| 6,063,098 | A | * | 5/2000 | Houser et al. ................. 606/169 |
| 6,146,392 | A | * | 11/2000 | Smith ............................. 606/147 |
| 6,322,570 | B1 | | 11/2001 | Matsutani et al. ............ 606/145 |
| 6,322,578 | B1 | | 11/2001 | Houle et al. ................... 606/205 |
| 6,666,854 | B1 | * | 12/2003 | Lange ................................ 606/1 |
| 2002/0088728 | A1 | | 7/2002 | Sugama ......................... 206/370 |
| 2002/0156497 | A1 | * | 10/2002 | Nagase et al. ................. 606/205 |
| 2003/0045833 | A1 | | 3/2003 | Murdoch |
| 2004/0260334 | A1 | * | 12/2004 | Braun ............................. 606/205 |

FOREIGN PATENT DOCUMENTS

| | | |
|---|---|---|
| EP | 0-661 022 A1 | 11/1994 |
| EP | 0 674 875 A1 | 2/1995 |
| EP | 1 748 734 B1 | 1/2008 |
| JP | 6-502354 | 3/1994 |
| JP | 07-143987 | 6/1995 |
| JP | 11-216145 | 8/1999 |
| JP | 2001-507972 | 6/2001 |
| JP | 2002-238910 | 8/2002 |
| NL | 1025852 | 10/2005 |
| WO | WO 92/05828 | 4/1992 |
| WO | WO 94/16628 | 8/1994 |
| WO | WO 98/30151 | 7/1998 |
| WO | WO 99/12480 | 3/1999 |
| WO | WO 2004/066848 | 12/2004 |

OTHER PUBLICATIONS

Office Action issued by the Japanese Patent Office on Nov. 16, 2010 in connection with corresponding Japanese Patent Application No. 2005-054020.

Search Report issued by European Patent Office on May 26, 2014 in connection with corresponding European application No. EP 05 73 9135.

Search Report issued by European Patent Office on Feb. 21, 2014 in connection with corresponding European application No. EP 05 73 9135.

* cited by examiner

SURGICAL INSTRUMENT

CROSS REFERENCE TO RELATED APPLICATION

This application is a divisional application of U.S. Ser. No. 11/403,037, filed on Apr. 12, 2006, which is a continuation application of PCT/JP2005/008484 filed on May 10, 2005 and claims benefit of Japanese Applications No. 2004-141513 filed in Japan on May 11, 2004 and No. 2005-054020 filed in Japan on Feb. 28, 2005, the entire contents of which are incorporated herein by this reference.

BACKGROUND OF THE INVENTION

1. Field of the Invention

The present invention relates to a surgical instrument used for operating a needle, etc. when cardiovascular tracts, urinary tracts, and tissues in body cavities are sutured.

2. Description of the Related Art

In recent surgery, a suturing operation has been performed to suture tissues while operating, e.g., a curved needle with a thread. In a surgical instrument for use in the suturing operation, a treatment portion is provided, for example, at the distal end of an insert section. When an anastomosis opening is sutured, a surgeon finely operates the needle by using the treatment portion of the surgical instrument to progress the suturing stitch by stitch with close attention. For that reason, the suturing operation in surgery has been a factor that prolongs the surgery time.

Particularly, in surgery to be performed within a limited space, e.g., in surgery using an endoscope, the insert section is generally inserted into a body cavity through a trocar or the like. Therefore, a lot of training is required until a surgeon has become able to operate the needle by using the treatment portion provided at the distal end of the insert section in a fine manner as intended.

For example, U.S. Pat. No. 5,810,877 discloses a surgical instrument for holding a needle, e.g., a suturing needle, used in anastomosing or suturing cardiovascular tracts and urinary tracts. The disclosed surgical instrument has a treatment portion of the so-called pincers structure and holds a needle by pinching it.

Also, U.S. Pat. No. 5,951,575 discloses a needle carrier aiming at improved convenience in use. When suturing blood vessels, organs, etc., the disclosed needle carrier enables a curved needle to be inserted by actively moving the needle following the curvature of the needle while the curved needle is grasped.

Further, U.S. Pat. No. 6,322,578 discloses a grasping forceps used in a body cavity for various applications, such as spreading tissues and handling threads.

The surgical instrument, the needle carrier, and the grasping forceps are each inserted into the body cavity through a trocar or the like. When the suturing operation is performed by using the needle carrier and the grasping forceps, the surgeon generally operates the needle carrier by one hand and operates the grasping forceps by the other hand.

In the suturing operation, the surgeon holds the proximal end of a needle by the needle carrier and places a needle tip at a predetermined position in an organ. Then, the surgeon actively moves the needle such that the needle is inserted in place. The tip of the needle inserted from the predetermined position in the organ passes through the organ and is projected out of the organ surface again. The surgeon holds the needle tip projected out of the organ by the needle carrier or the grasping forceps and then draws the needle out of the organ by making an operation at hand. One stitch of suturing is thus completed.

When drawing out the needle by the needle carrier, the surgeon temporarily releases the proximal end of the needle from the held state. Thereafter, the surgeon moves the needle carrier from the proximal end to the tip of the needle and draws out the needle by holding the needle tip with the needle carrier.

On the other hand, when drawing out the needle by using the grasping forceps, the surgeon first inserts the needle while operating the needle carrier by one hand. Then, the surgeon grasps the needle tip and draws out the needle while operating the grasping forceps by the other hand. By thus inserting the needle with the needle carrier and drawing out the needle with the grasping forceps, the needle can be more smoothly drawn out and the suturing operation can be finished in a shorter time than the case of inserting and drawing out the needle with only the needle carrier.

When the needle inserted in, e.g., a luminal tissue is drawn out, the needle requires to be moved following the curved shape of the needle so as to avoid the tissue from being damaged. In the surgery using an endoscope, however, a region in which the treatment portion is allowed to move is limited. Let us now look at a manual operation of drawing out a suturing needle 33 in the form of a curved needle inserted in a first luminal organ 31 and a second luminal organ 32 as shown in FIG. 1, for example, by using a grasping forceps 34.

First, the surgeon introduces the grasping forceps 34 into a body cavity through a trocar 36 stuck in a patient body wall 35. In this state, the grasping forceps 34 is restricted in its movable region other than the direction in which it is advanced and retracted with respect to the trocar 36. Numeral 37 denotes a portion which has been sutured, 38 denotes a suturing thread, and 39 denotes an opening to be sutured.

Then, as shown in FIG. 2, the surgeon grasps a needle tip 33a by the grasping forceps 34 introduced through the trocar 36. From that state, the surgeon may try to draw out the suturing needle 33, for example, by moving the grasping forceps 34 to pull it outward of the patient body wall 35 as indicated by an arrow A. However, when the needle is drawn out in such a manner, a tensile force is applied from the suturing needle 33 to the luminal organ 32 as indicated by an arrow B in FIG. 3, thus resulting in a risk that the suturing needle 33 cannot be easily drawn out.

SUMMARY OF THE INVENTION

In a surgical instrument of the present invention, a treatment portion continuously provided at a distal end of an insert section has a needle holding member made of an elastic body capable of holding a needle when the needle is pierced into the elastic body.

DETAILED DESCRIPTION OF THE PREFERRED EMBODIMENTS

Embodiments of the present invention will be described below with reference to the drawings.

A first embodiment will be described with reference to FIGS. 4 through 8.

Figure 1:
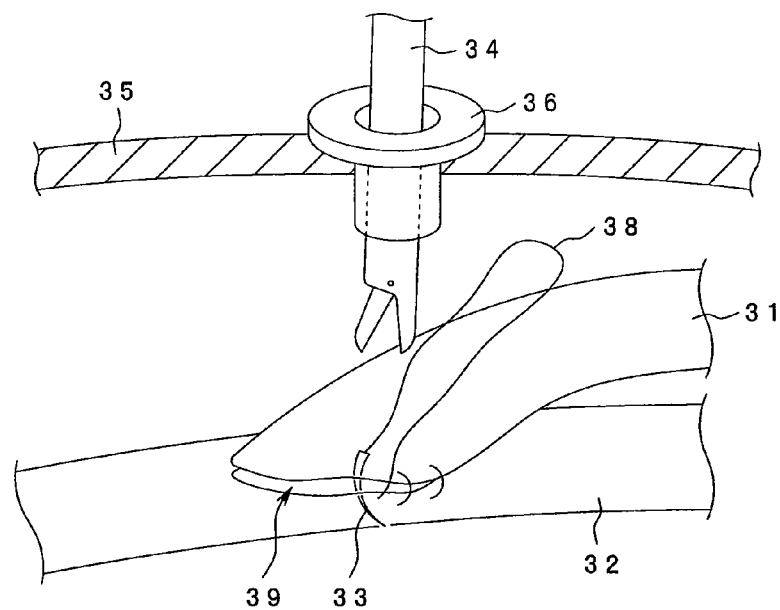
FIG. 1 is an illustration for explaining a grasping forceps introduced into a body cavity through a trocar and a suturing needle operated by the grasping forceps in the body cavity.
Figure 2:
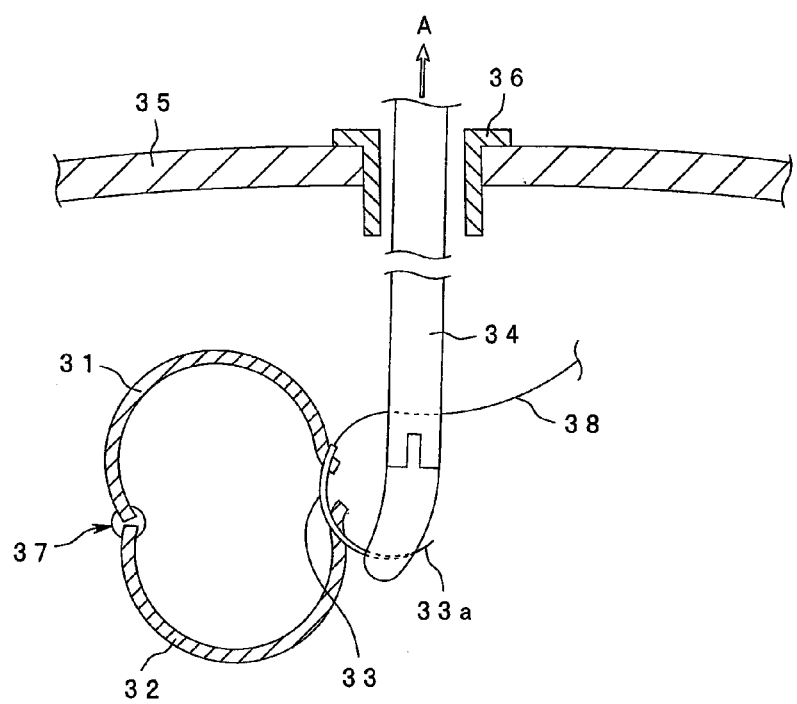
FIG. 2 is an illustration for explaining a state where the suturing needle inserted in luminal organs is grasped by the grasping forceps and the grasping forceps is pulled out of the body cavity.
Figure 3:
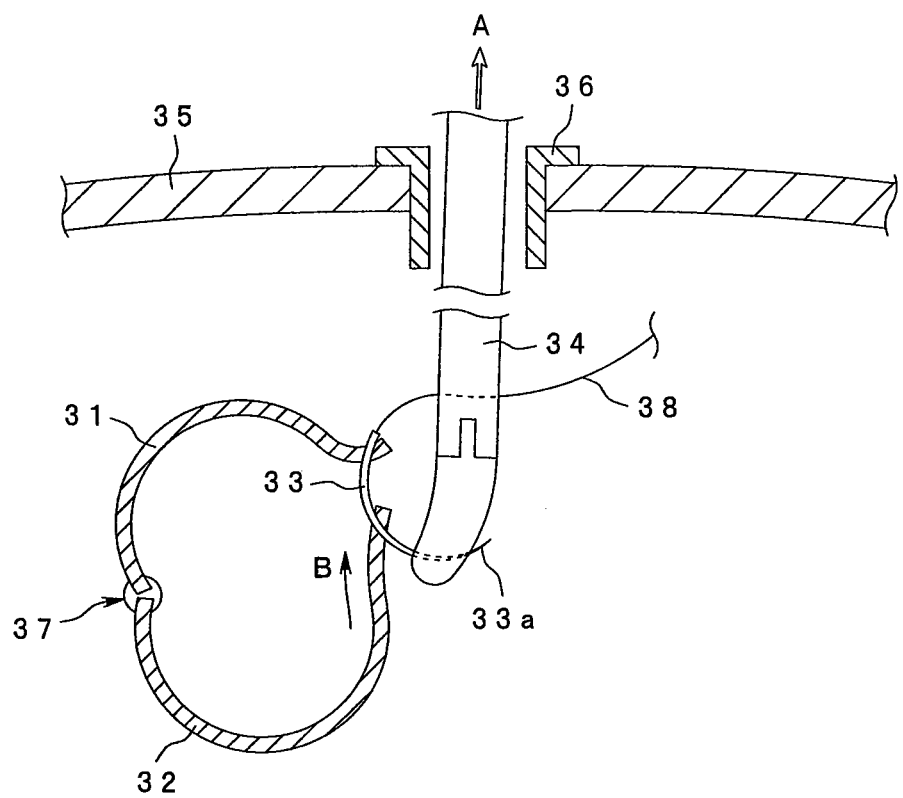
FIG. 3 is an illustration showing the state where a tensile force is imposed on the luminal organ from the suturing needle in the body cavity which is drawn out by using the grasping forceps.
Figure 4:
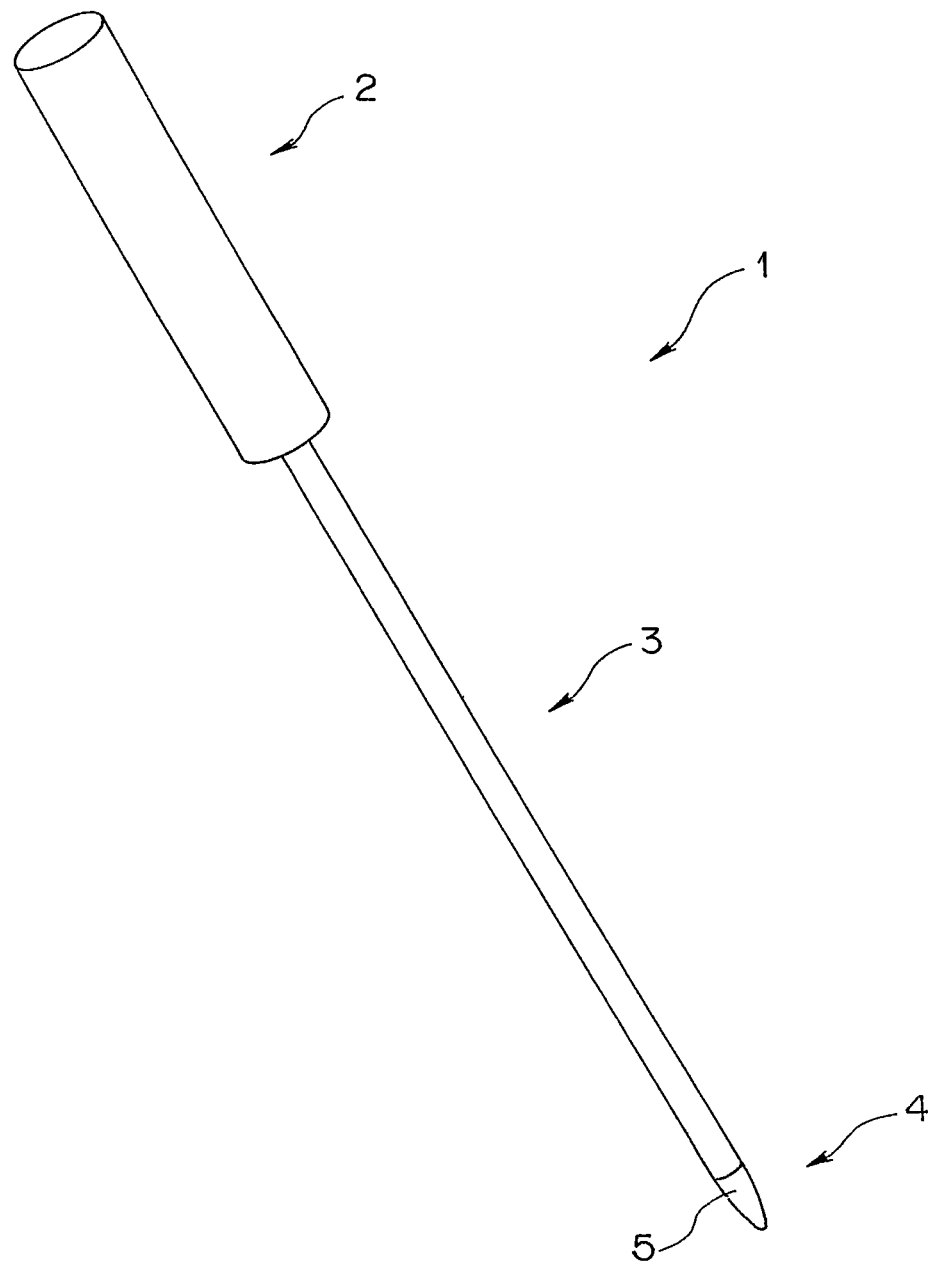
FIG. 4 is a perspective view showing the general construction of a surgical instrument according to a first embodiment.

In FIG. 4, numeral 1 denotes a surgical instrument capable of holding, e.g., a later-described curved needle for suturing (see numeral 6 in FIG. 5 and other figures, hereinafter referred to simply as a "needle") when cardiovascular tracts, urinary tracts, etc. are anastomosed or sutured.

The surgical instrument 1 includes an operating section 2 gasped by one hand of a surgeon for operating the surgical instrument 1. An insert section 3 is continuously provided at the distal end side of the operating section 2. A treatment portion 4 as an essential portion is continuously provided at the distal end side of the insert section 3.

The operating section 2 and the insert section 3 are integrally formed of, e.g., a stainless rod member. The insert section 3 is formed to have an outer diameter smaller than that of the operating section 2. More specifically, the insert section 3 is formed in such a thickness as being able to be inserted through a trocar used in surgery using an endoscope. The surgical instrument 1 is therefore usable in any of the surgery using an endoscope and an abdominal operation, i.e., the so-called open surgery.

The operating section 2 and the insert section 3 may be formed of the so-called engineering plastic, such as polycarbonate or PEEK. Also, the outer diameter of the operating section 2 and the outer diameter of the insert section 3 may be of course equal to each other. The operating section 2 is preferably subjected to a non-slipping process. Examples of the non-slipping process include knurling and sand blasting.

A needle holding member 5 serving as needle holding means, which constitutes the treatment portion 4, is fixed to the distal end of the insert section 3 by fusion, for example. The needle holding member 5 is formed by shaping an elastic body made of, e.g., silicone rubber into a substantially conical tapered form, for example. The needle 6 is held by the needle holding member 5 upon insertion of the needle 6 into the needle holding member 5, namely when the needle 6 is pierced into the elastic body.

The shape of the needle holding member 5 is not limited to the substantially conical tapered form, and the needle holding member 5 can be shaped into any of other various forms, such as substantially spherical, columnar, poly-angular pyramidal, or poly-angular pillar form. Also, the needle holding member 5 can be made of any of various materials, such as fluorine-contained rubber, polyvinyl chloride, or polyurethane. By properly selecting the material, the hardness of the needle holding member 5 can be properly set such that an elastic force is changed and the needle holding member 5 is able to hold the needle 6 in the pierced state by an optimum holding force.

In use of the surgical instrument 1 thus constructed, the surgeon can perform various operations, such as lifting and pushing apart tissues in a surgery field, by grasping the operating section 2 by one hand and changing the position of the treatment portion 4.

Figure 5:
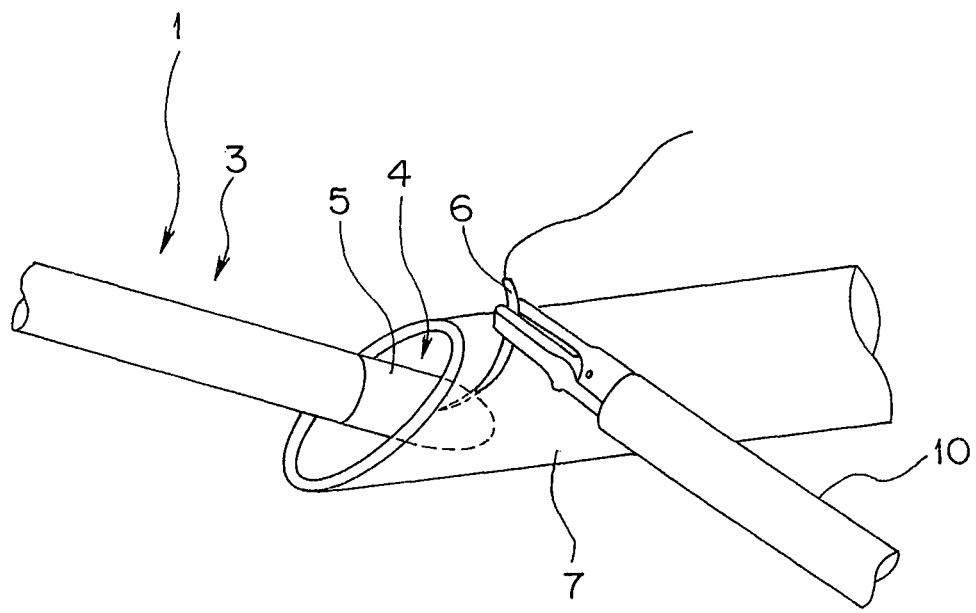
FIG. 5 is an explanatory view showing the operation of transferring a needle from a needle carrier to a needle holding member.
Figure 6:
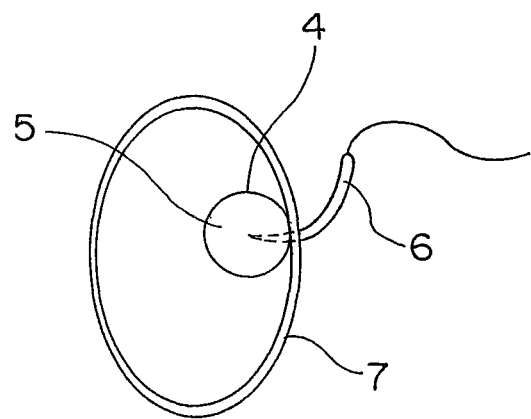
FIG. 6 is an explanatory view of the needle holding member holding the needle in a blood vessel.

As shown in FIG. 5, the surgeon sutures a blood vessel 7 while operating a needle carrier 10 by one hand and operating the surgical instrument 1 by the other hand. In such a case, the surgeon pierces the tip of the needle 6 held by the needle carrier 10 into the needle holding member 5 in any desired direction. With that operation, the needle 6 can be transferred to the surgical instrument 1. In particular, as shown in FIGS. 5 and 6, when the needle 6 held by the needle carrier 10 is used to stitch the blood vessel 7, the needle holding member 5 is inserted through an opening of the blood vessel 7 and is pressed against an inner wall of the blood vessel 7 near a point where the needle 6 is pierced. This makes it possible to support the blood vessel 7 by the surgical instrument 1 and to receive the needle 6 by the surgical instrument 1 at the same time. When the needle 6 is pierced into the blood vessel 7 from the inner wall side toward the outer side, the surgical instrument 1 can also support the blood vessel 7 and receive the needle 6 at the same time.

Figure 7:
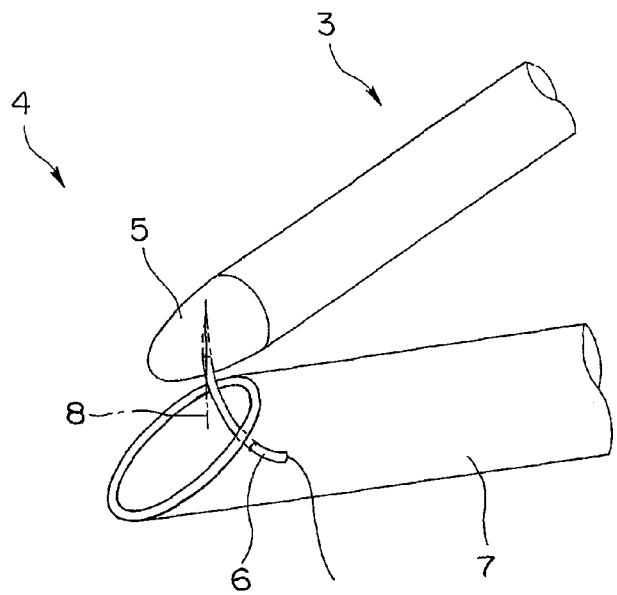
FIG. 7 is an explanatory view for explaining the state where the needle is held by the needle holding member in the stitching operation with the surgical instrument.
Figure 8:
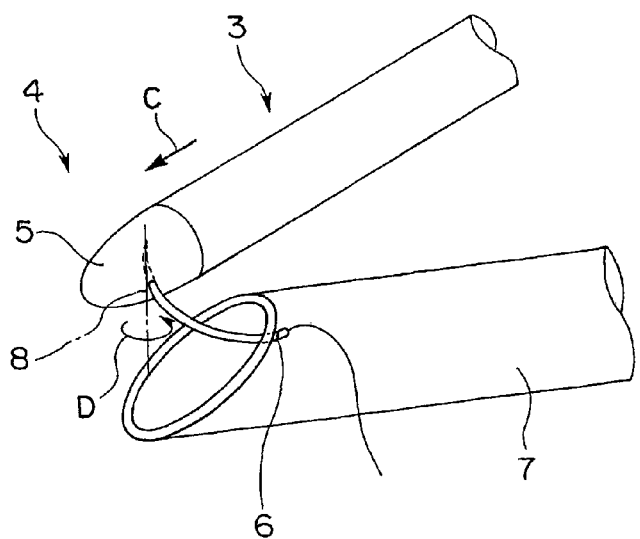
FIG. 8 is an explanatory view for explaining the state where the needle is rotated corresponding to a force applied from a body tissue in a position, at which the needle is pierced into the tissue, by moving an insert section in the stitching operation with the surgical instrument.

As shown in FIGS. 7 and 8, the needle 6 held by the needle holding member 5 is rotatable about an axis 8 passing the point where the needle 6 is pierced into the needle holding member 5. Therefore, for example, when the needle 6 pierced through the blood vessel 7 is drawn out by using the surgical instrument 1, the needle 6 is allowed to passively rotate corresponding to a force applied from the blood vessel 7. As shown in FIG. 8, for example, when the needle holding member 5 is moved to advance in a direction indicated by an arrow C in the figure, the needle 6 is rotated about the axis 8 of rotation in a direction indicated by an arrow D in the FIGURE corresponding to the force applied from the position of the blood vessel 7 where the needle 6 is pierced.

Thus, the surgical instrument of this embodiment is constructed so as to hold the needle by the needle holding member with the needle pierced into the latter. It is therefore possible not only to stably place the treatment portion at any desired position, but also to easily transfer the needle without requiring the open/close operation for holding the needle unlike, e.g., the known needle carrier of the pincers structure. Particularly, operability in transferring the needle is markedly improved in such fine operations as suturing thin tracts, e.g., cardiovascular tracts and urinary tracts.

Also, the needle can be pierced into the needle holding member from various directions regardless of the posture of the surgical instrument. Therefore, operability in receiving the needle from the needle carrier, etc. is further improved. This feature is particularly effective in the surgery using the endoscope in which the allowable posture of the surgical instrument 1 is limited.

Further, when the needle pierced through the tissue, e.g., the blood vessel, is held and drawn out by the needle holding member, the needle is allowed to passively rotate corresponding to the force imposed on the needle from the tissue. Accordingly, satisfactory stitching operation can be realized without exerting a large tension on the tissue.

When the needle is pierced into the tissue, e.g., the blood vessel, by using the needle carrier or the like, holding of the tissue and receiving of the needle can be performed at the same time with one instrument by placing the needle holding member at the backside of the point where the needle is pierced. Accordingly, a series of operations from a step of piercing the needle into the tissue to a step of drawing out the needle can be quickly performed while the number of the treatment instruments used can be reduced. As a result, in the surgery using the endoscope, it is possible to reduce the number of ports to be incised in the patient body for insertion of the treatment instruments, and to realize less-invasive surgery.

Moreover, in the state where the needle is held by the needle holding member, the needle tip is buried in the needle holding member. This not only prevents the needle tip from damaging the tissue, but also prevents the needle tip from contacting with the other surgical instrument and from causing a trouble.

A second embodiment of the present invention will be described below with reference to FIGS. 9 and 10.

This second embodiment differs from the above-described first embodiment in adding the function of variably adjusting the force of holding the needle, which is applied from the needle holding member. Similar components to those in the first embodiment are denoted by the same numerals and a description of those components is omitted here.

Figure 9:
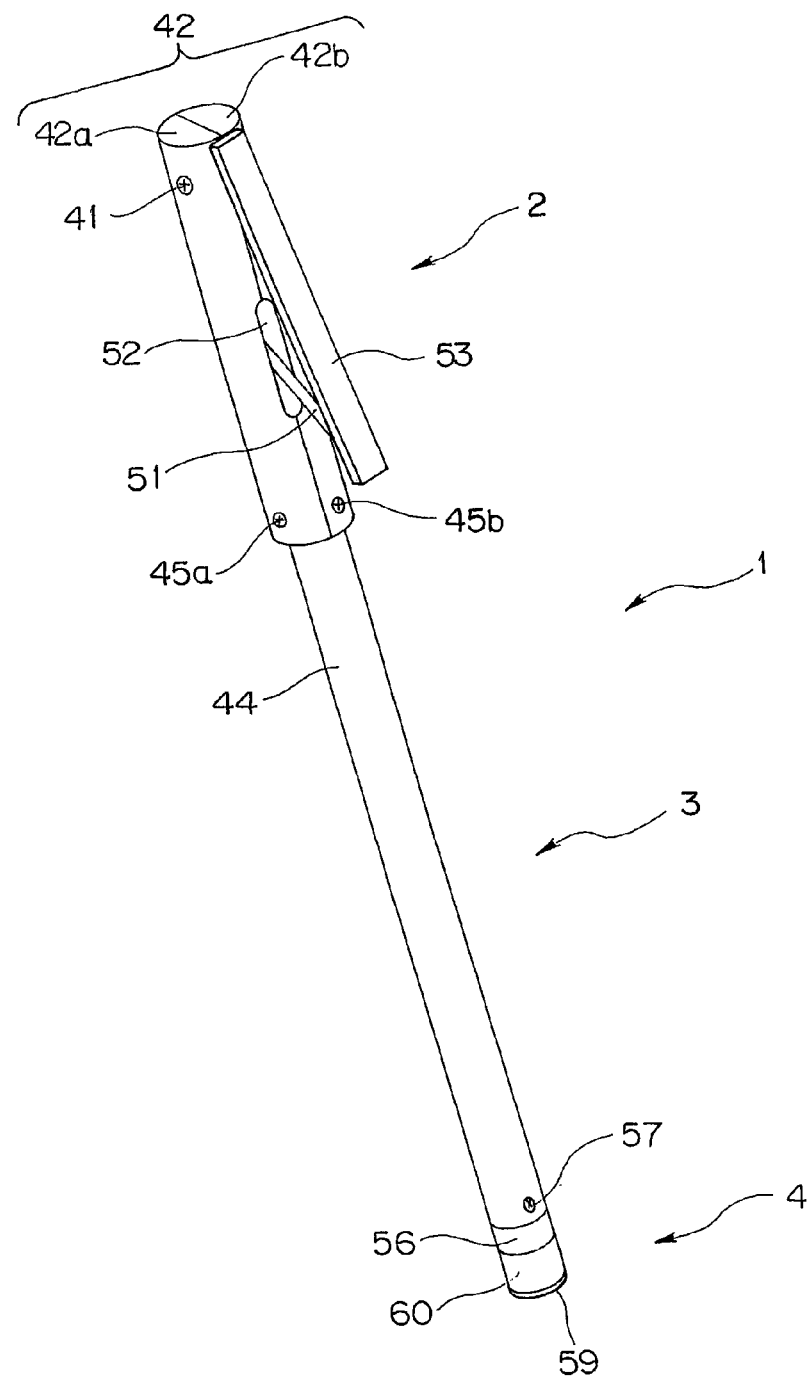
FIG. 9 is a perspective view showing the general construction of a surgical instrument according to a second embodiment.
Figure 10:
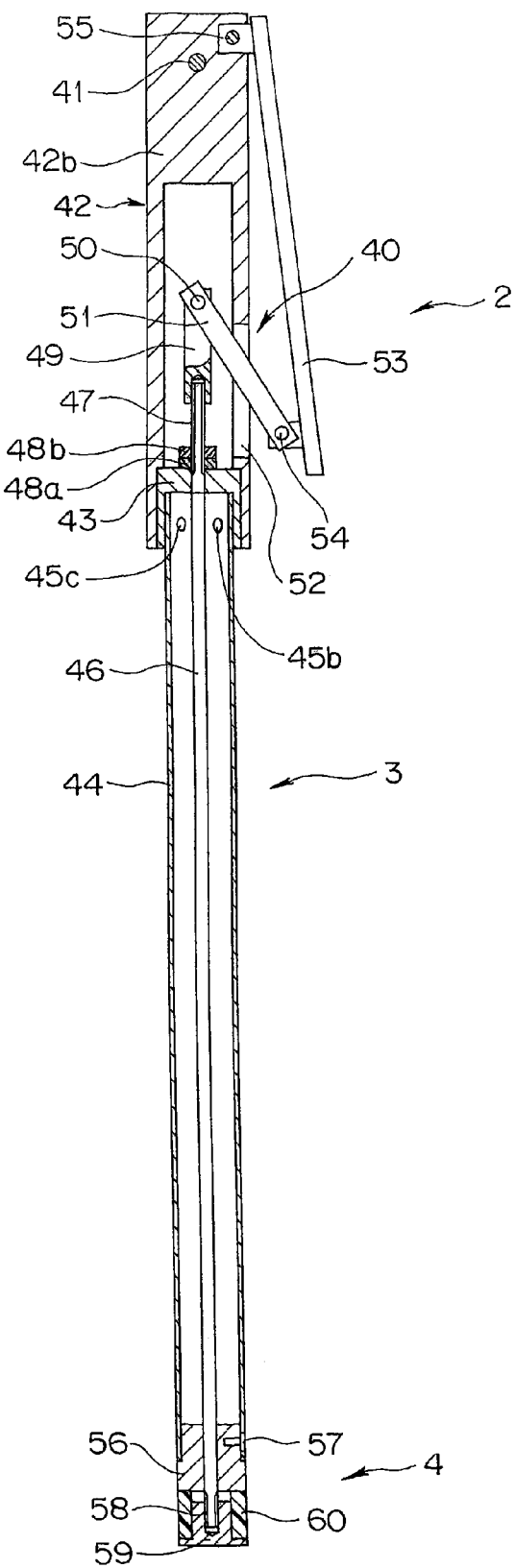
FIG. 10 is a longitudinal sectional view for explaining the construction of a surgical instrument.

In this embodiment, as shown in FIGS. 9 and 10, an operating section 2 has a handle portion 42 incorporating a link mechanism 40. The handle portion 42 is constructed by a pair of handle portion halves 42a and 42b coupled to each other by a screw 41. A slide bearing 43 for supporting the proximal end side of a later-described rod 46, which penetrates through the slide bearing 43, is disposed at the distal end of the handle portion 42.

A hollow outer sleeve 44 constituting an insert section 3 is fitted at its proximal end portion to an inner periphery of the slide bearing 43. The handle portion 42, the slide bearing 43, and the outer sleeve 44 are fixedly fastened together, for example, by screws 45a, 45b and 45c which are disposed on the same circumference at angular intervals of 120°.

As shown in FIG. 10, a threaded portion 47 is formed in a proximal region of the rod 46, which penetrates through the slide bearing 43 and is exposed to an inner space of the handle portion 42. Nuts 48a and 48b are screwed over the threaded portion 47. The presence of those nuts limits movement of the rod 46 toward the distal end side. The distal end of a joint 49 is screwed with the proximal end of the threaded portion 47. One end of an arm 51 is rotatably coupled to the proximal end of the joint 49 through a pin 50.

An opening 52 is formed in a joint area between the handle portion halves 42a and 42b. The other end of the arm 51 is extended through the opening 52 and is exposed to the outside. A free end of a lever 53 is rotatably coupled to the other end of the arm 51 through a pin 54. A fixed end of the lever 53 is swingably supported by a pin 55 which is buried in the proximal end side of the handle portion halves 42a and 42b.

With such an arrangement, in the operating section 2, the link mechanism 40 is constituted which is capable of advancing and retracting the rod 46 in the outer sleeve 44 in response to the lever 53 being turned up and down with respect to the handle portion 42.

On the other hand, a slide bearing 56 for supporting the rod 46, which penetrates through the slide bearing 56, is fixed to the distal end of the outer sleeve 44 by a screw 57. A threaded portion 58 is formed in a distal end region of the rod 46, which penetrates through the slide bearing 56 and is exposed to the same side as a treatment portion 4. A cap 59 is screwed over the threaded portion 58. A needle holding member 60 serving as needle holding means, which is made of an elastic body having a substantially cylindrical shape, is sandwiched between the cap 59 and the slide bearing 56. The elastic body constituting the needle holding member 60 is made of, e.g., silicone rubber, fluorine-contained rubber, polyvinyl chloride, or polyurethane.

In use of the surgical instrument thus constructed, when the lever 53 is turned down by the surgeon grasping the operating section 2, the rod 46 is moved toward the proximal end side together with the joint 49 through the arm 51. Correspondingly, the needle holding member 60 sandwiched between the slide bearing 56 and the cap 59 is compressed. As a result of the needle holding member 60 being compressed and elastically deformed, the force of holding the needle 6 applied by the needle holding member 60 is increased. Thus, with this embodiment, the link mechanism 40 disposed in the operating section 2 and the cap 59 interlocked with the link mechanism 40 jointly realize a needle holding force adjusting mechanism for elastically deforming the needle holding member 60 and variably adjusting the force of holding the needle 6.

Usually, the adjustment of the holding force of the needle holding member 60 is performed after, e.g., transfer of the needle 6. Therefore, operability in, for example, transferring the needle 6 from the needle carrier 10 to the surgical instrument 1 can be maintained satisfactory.

In addition to substantially the same advantages as those obtained with the first embodiment, this second embodiment can provide an advantage that the needle can be held with higher reliability by compressing the needle holding member so as to increase the force of holding the needle pierced into the needle holding member.

A third embodiment of the present invention will be described below with reference to FIGS. 11 through 13.

This third embodiment differs from the above-described first embodiment in the construction of a treatment portion 4. The other similar components to those in the first embodiment are denoted by the same numerals and a description of those components is omitted here.

Figure 11:
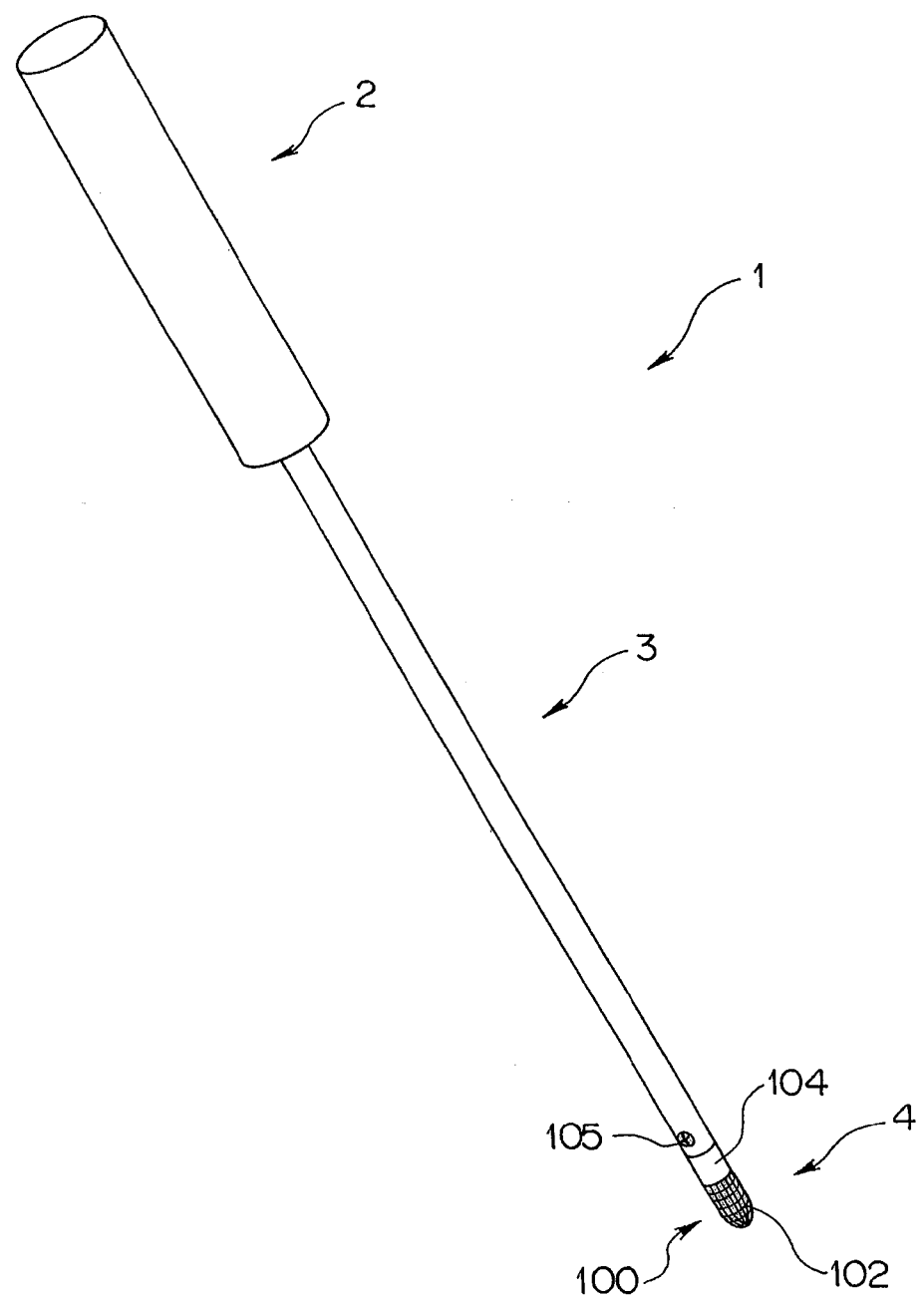
FIG. 11 is a perspective view showing the general construction of a surgical instrument according to a third embodiment.
Figure 12:
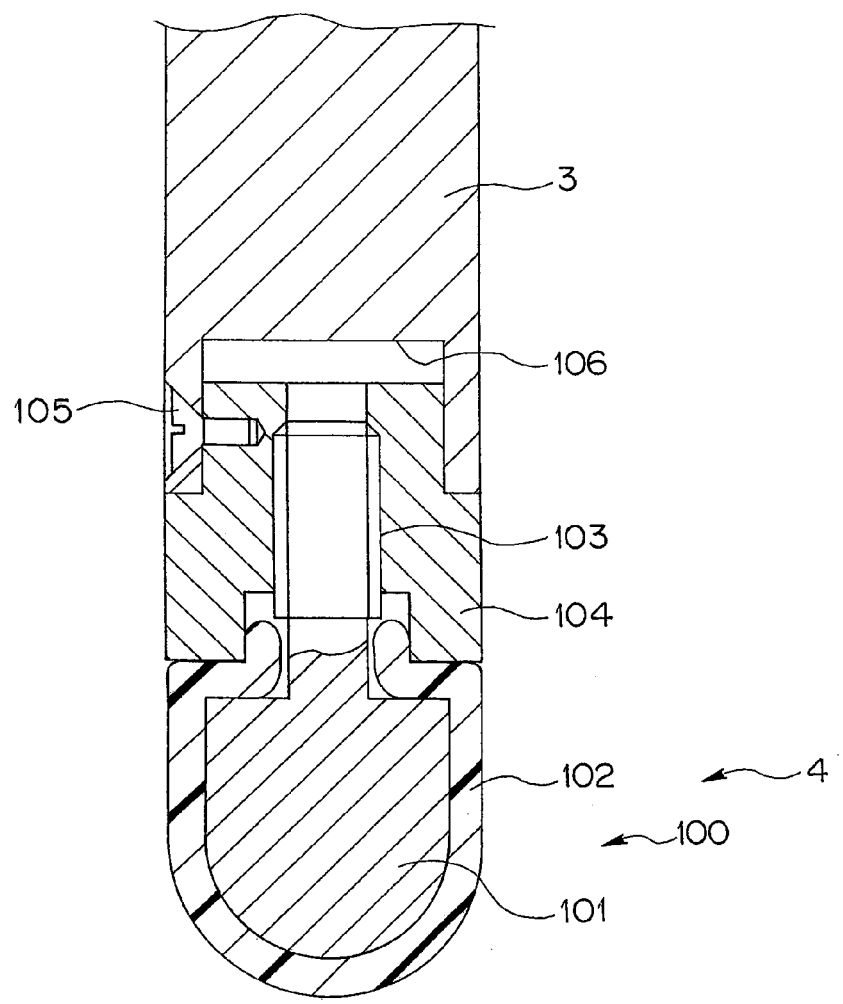
FIG. 12 is a longitudinal sectional view for explaining the construction of a treatment portion.
Figure 13:
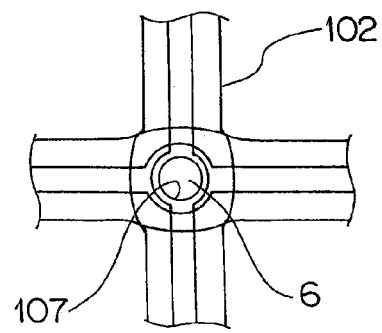
FIG. 13 is an illustration for explaining an elastic body.

In this embodiment, as shown in FIGS. 11 and 12, a needle holding member 100 serving as needle holding means, which is disposed in a treatment portion 4, comprises an end cap 101 and an elastic body 102 covering the surface of the end cap 101. The end cap 101 is coupled to the distal end of an insert section 3 through a connector 104.

A recess 106 is formed at the distal end of the insert section 3, and a base portion of the connector 104 is fitted to the recess 106. A screw 105 penetrating from the lateral side of the insert section 3 into the recess 106 is screwed into the base portion of the connector 104. With such an arrangement, the connector 104 is coupled to and held by the insert section 3.

A threaded hole is formed in the connector 104 to penetrate its center in the axial direction. A threaded portion 103 projecting from a base portion of the end cap 101 is screwed into the threaded hole. When the end cap 101 is coupled to the connector 104 by screwing the threaded portion 103 into the threaded hole, a peripheral edge of the elastic body 102 is tucked between the end cap 101 and the connector 104. The elastic body 102 is thereby held on the surface of the end cap 101.

The elastic body 102 is made of an elastic member having a plurality of holes 107 which have a smaller diameter than that of the needle 6 and are arrayed in a mesh-like pattern. As shown in FIG. 13, when the needle 6 is pierced into the hole 107, the needle 6 is held in the hole 107 by an elastic restoring force (contractive force) applied from the hole 107.

In addition to substantially the same advantages as those obtained with the first embodiment, this third embodiment can provide an advantage that, since the end cap and the elastic body can be easily removed from the connector, the deteriorated elastic body can be easily replaced and a cost reduction can be realized.

A fourth embodiment of the present invention will be described below with reference to FIGS. 14 through 18.

This fourth embodiment differs from the above-described first embodiment in adding the function of variably adjusting the force of holding the needle, which is applied from the needle holding member. The other similar components to those in the first embodiment are denoted by the same numerals and a description of those components is omitted here.

Figure 14:
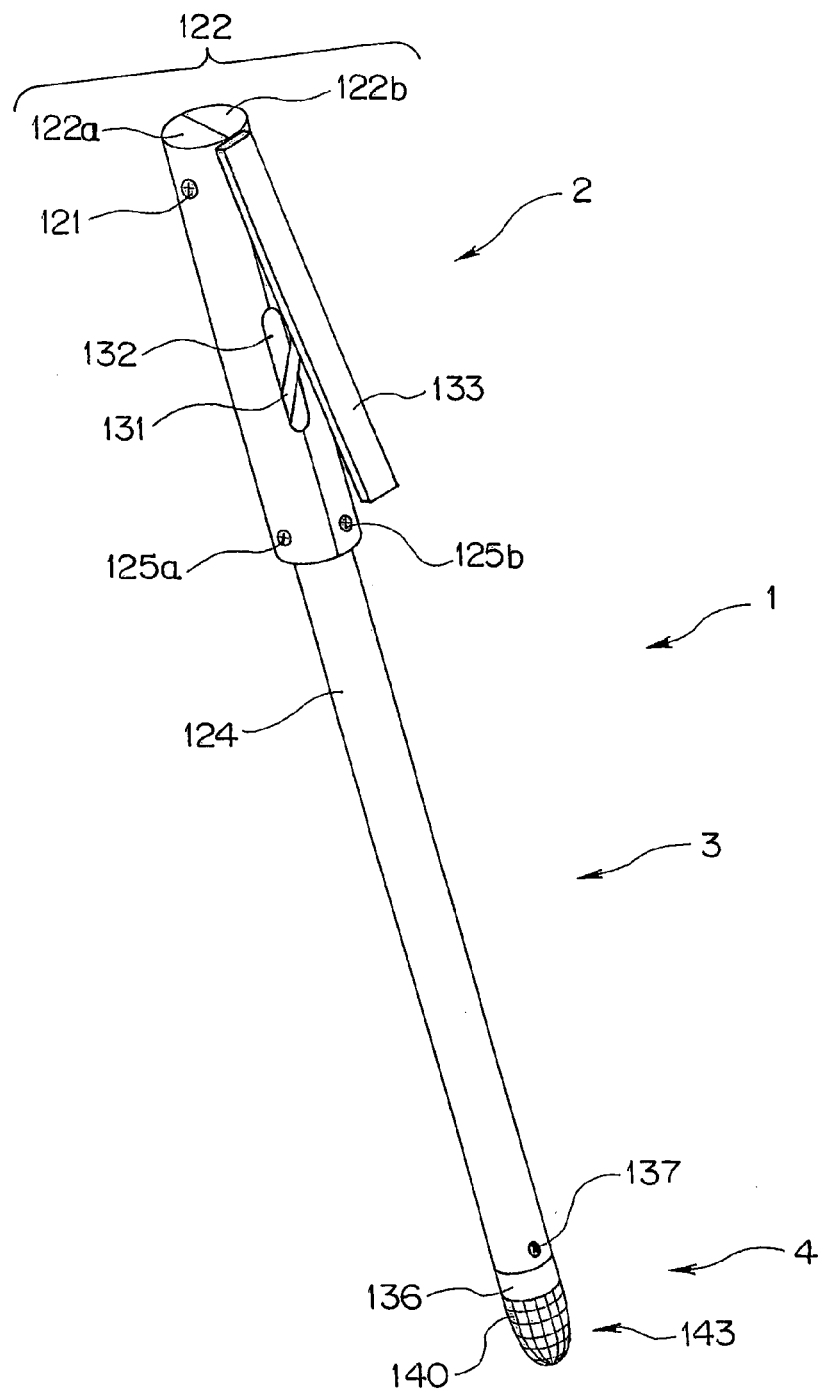
FIG. 14 is a perspective view showing the general construction of a surgical instrument according to a fourth embodiment.
Figure 15:
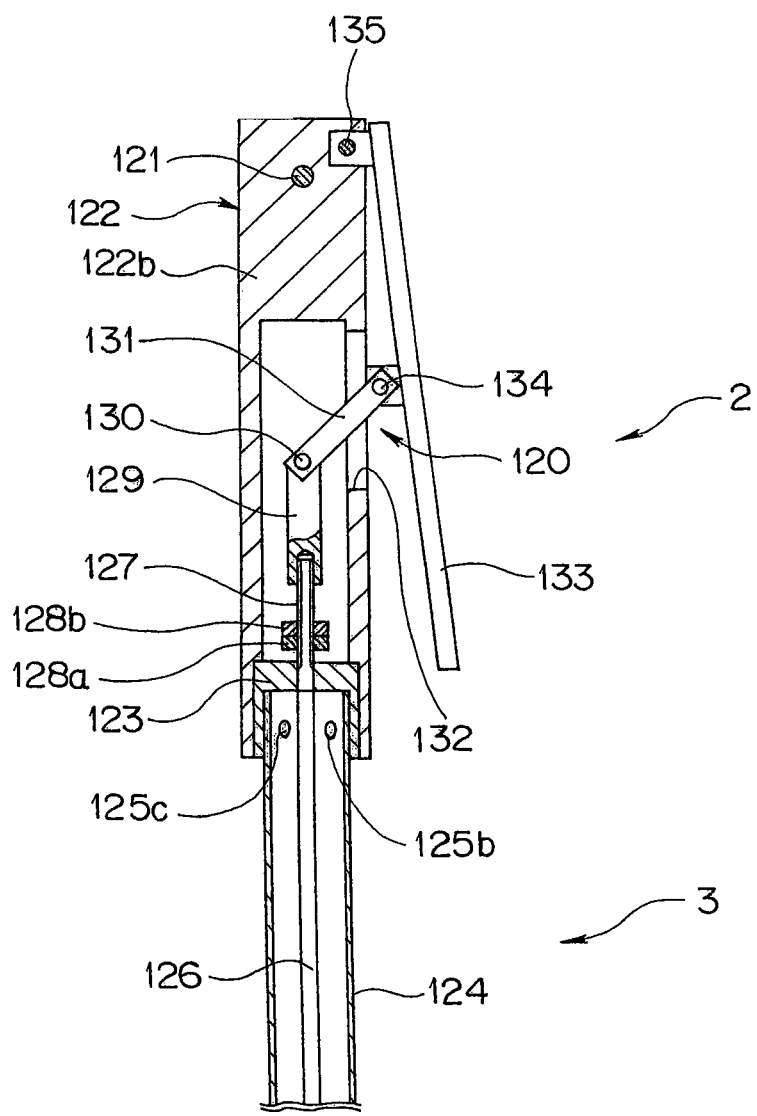
FIG. 15 is a longitudinal sectional view for explaining the construction of an operating section.

In this embodiment, as shown in FIGS. 14 and 15, an operating section 2 has a handle portion 122 incorporating a link mechanism 120. The handle portion 122 is constructed by a pair of handle portion halves 122a and 122b coupled to each other by a screw 121. A slide bearing 123 for supporting the proximal end side of a later-described rod 126, which penetrates through the slide bearing 123, is disposed at a distal end of the handle portion 122.

A hollow outer sleeve 124 constituting an insert section 3 is fitted at its proximal end portion to an inner periphery of the slide bearing 123. The handle portion 122, the slide bearing 123, and the outer sleeve 124 are fixedly fastened together, for example, by screws 125a, 125b and 125c which are disposed on the same circumference at angular intervals of 120°.

As shown in FIG. 15, a threaded portion 127 is formed in a proximal region of the rod 126, which penetrates through the slide bearing 123 and is exposed to an inner space of the handle portion 122. Movement of the rod 126 toward the distal end side is limited by nuts 128a and 128b which are screwed over the threaded portion 127.

The distal end of a joint 129 is screwed over the proximal end of the threaded portion 127. One end of an arm 131 constituting the link mechanism 120 is rotatably coupled to the proximal end of the joint 129 through a pin 130.

An opening 132 is formed in a joint area between the handle portion halves 122a and 122b. The other end of the arm 131 is extended through the opening 132 and is exposed to the outside. An intermediate portion of a lever 133 is rotatably coupled to the other end of the arm 131 through a pin 134. A fixed end of the lever 133 is swingably supported by a pin 135 which is buried in the proximal end side of the handle portion halves 122a and 122b.

With such an arrangement, in the operating section 2, the link mechanism 120 is constituted which is capable of advancing and retracting the rod 126 in the outer sleeve 124 in response to the lever 133 being turned up and down with respect to the handle portion 122.

Figure 16:
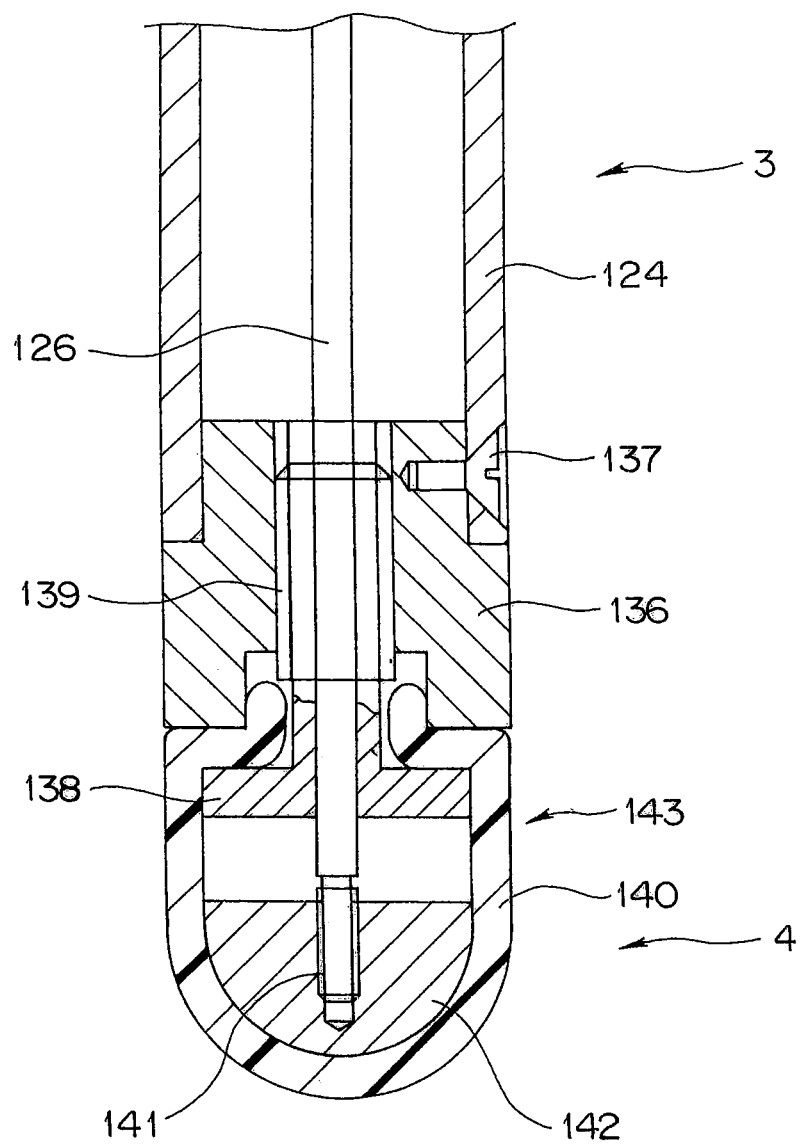
FIG. 16 is a longitudinal sectional view for explaining the construction of a treatment portion.

On the other hand, as shown in FIG. 16, a connector 136 is fixed to the distal end of the outer sleeve 124 by a screw 137. A threaded hole is formed in the connector 136 to penetrate its center in the axial direction. A slide bearing 138 for supporting the rod 126, which penetrates through the slide bearing 138, is coupled to the connector 136 by screwing into the threaded hole.

More specifically, a threaded portion 139 having a through hole formed therein is projected from the slide bearing 138. The threaded portion 139 is screwed into the threaded hole of the connector 136, whereby the slide bearing 138 is coupled to the connector 136.

A threaded portion 141 is formed in a distal end region of the rod 126, which penetrates through the slide bearing 138 and is exposed to the same side as a treatment portion 4. An end pusher 142 is screwed over the threaded portion 141. The end pusher 142 is covered with an elastic body 140 constituting a needle holding member 143, which serves as needle holding means.

When the slide bearing 138 and the connector 136 are coupled to each other by screwing the threaded portion 139 into the threaded hole, a peripheral edge of the elastic body 140 is tucked between the slide bearing 138 and the connector 136. The elastic body 140 is thereby held on the surface of the end pusher 142.

Figure 17:
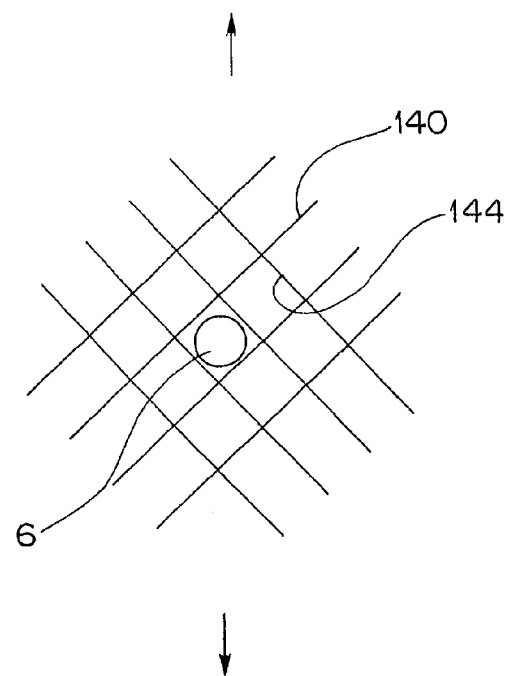
FIG. 17 is an illustration for explaining an elastic body in an ordinary state.

As shown in FIG. 17, the elastic body 140 is made of an elastic member having a plurality of holes 144 into which the needle 6 can be pierced and which are arrayed in a mesh-like pattern. The elastic body 140 is preferably made of, e.g., silicone rubber, fluorine-contained rubber, polyvinyl chloride, or polyurethane.

Figure 18:
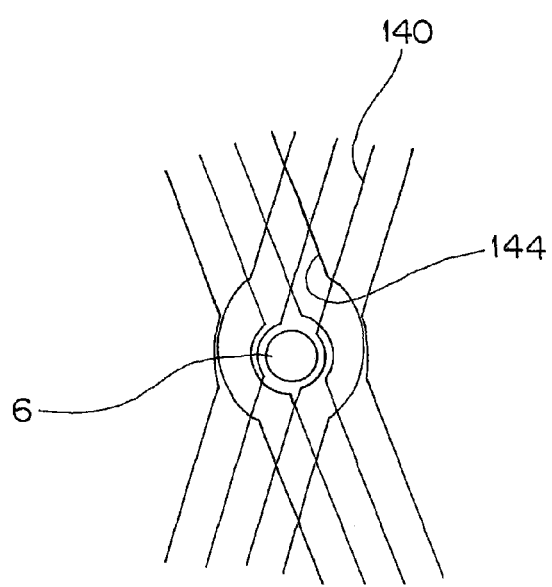
FIG. 18 is an illustration for explaining the elastic body when the elastic body is elastically deformed.

In use of the surgical instrument thus constructed, when the lever 133 is turned down by the surgeon grasping the operating section 2, the rod 126 is moved toward the distal end side together with the joint 129 through the arm 131. Correspondingly, the end pusher 142 is also moved toward the distal end side. With the movement of the end pusher 142 toward the distal end side, the elastic body 140 covering the end pusher 142 is pulled outward of the distal end side. The holes 144 of the elastic body 140 are elastically deformed by a tension caused upon the elastic body 140 being thus pulled outward. Accordingly, as shown in FIG. 18, the force of holding the needle 6 applied by the needle holding member 143 is increased. Thus, with this embodiment, the link mechanism 120 disposed in the operating section 2 and the end pusher 142 interlocked with the link mechanism 120 jointly realize a needle holding force adjusting mechanism for elastically deforming the elastic body 140 and variably adjusting the force of holding the needle 6.

Usually, the adjustment of the holding force of the needle holding member 143 is performed after, e.g., transfer of the needle 6. Therefore, operability in, for example, transferring the needle 6 from the needle carrier 10 to the surgical instrument 1 can be maintained satisfactory.

In addition to substantially the same advantages as those obtained with the first embodiment, this fourth embodiment can provide an advantage that the needle can be held with higher reliability because the force of holding the needle pierced into the hole can be increased by the outward pulling of the needle holding member.

A fifth embodiment of the present invention will be described below with reference to FIG. 19.

This fifth embodiment differs from the above-described first embodiment in that a plurality of cutouts are formed in a needle holding member. The other similar components to those in the first embodiment are denoted by the same numerals and a description of those components is omitted here.

Figure 19:
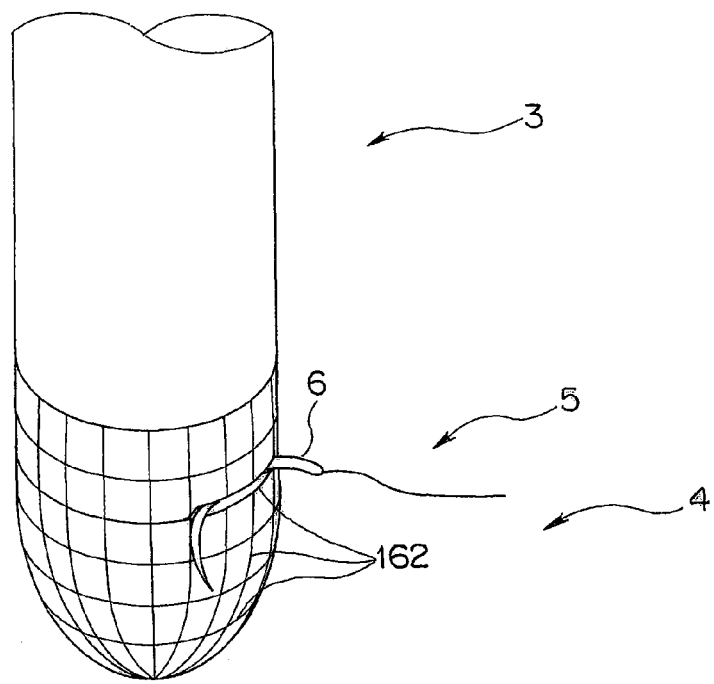
FIG. 19 is a perspective view for explaining the construction of a treatment portion of a surgical instrument according to a fifth embodiment.

As shown in FIG. 19, a needle holding member 5 constituting a treatment portion 4 has a plurality of cutouts 162 formed, for example, in the circumferential direction and the longitudinal axial direction.

With such a construction, for example, when the needle 6 is transferred from the needle carrier 10 to the surgical instrument 1, the needle 6 is inserted into and caught by one of the cutouts 162. Thus, the needle 6 can be held by the needle holding member 5 without piercing the needle tip into the needle holding member 5. Of course, the needle 6 can also be held by the needle holding member 5 by piercing the needle tip into other portion of the needle holding member 5 than the cutouts 162.

In addition to substantially the same advantages as those obtained with the first embodiment, this fifth embodiment can provide an advantage that, because of no need of piercing the needle into the needle holding member, the operation necessary for holding the needle on the needle holding member is facilitated and operability can be further improved. Moreover, since the cutout is able to hold the needle at other portion than the tip, even higher operability can be realized.

A sixth embodiment of the present invention will be described below with reference to FIG. 20.

This sixth embodiment differs from the above-described first embodiment in that a needle holding member is covered with an adhesive layer. The other similar components to those in the first embodiment are denoted by the same numerals and a description of those components is omitted here.

Figure 20:
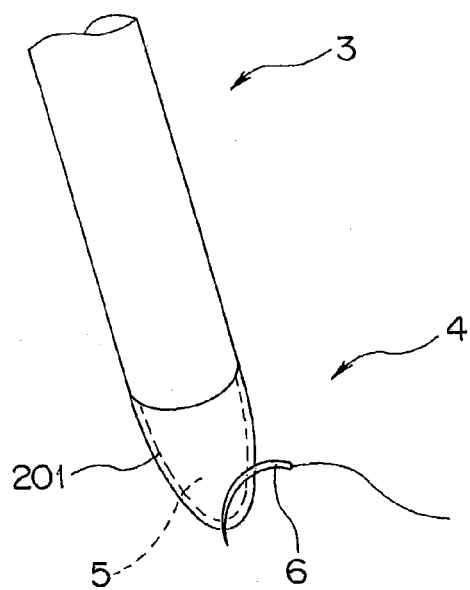
FIG. 20 is a perspective view for explaining the construction of a treatment portion of a surgical instrument according to a sixth embodiment.

As shown in FIG. 20, an adhesive layer 201 is formed on the surface of a needle holding member 5 constituting a treatment portion 4.

With such a construction, for example, when the needle 6 is transferred from the needle carrier 10 to the surgical instrument 1, the needle 6 is brought into contact with the adhesive layer 201. Thus, the needle 6 can be held by the surface of the needle holding member 5 without piercing the needle tip into the needle holding member 5. Of course, the needle 6 can also be held by the needle holding member 5 by piercing the needle tip into the needle holding member 5.

In addition to substantially the same advantages as those obtained with the first embodiment, this sixth embodiment can provide an advantage that, because of no need of piercing the needle into the needle holding member, the operation necessary for holding the needle on the needle holding member is facilitated and operability can be further improved. Moreover, since the adhesive layer is able to hold the needle at other portion than the tip, even higher operability can be realized.

A seventh embodiment of the present invention will be described below with reference to FIG. 21.

This seventh embodiment differs from the above-described first embodiment in that a needle holding member includes a magnet disposed inside an elastic body. The other similar components to those in the first embodiment are denoted by the same numerals and a description of those components is omitted here.

Figure 21:
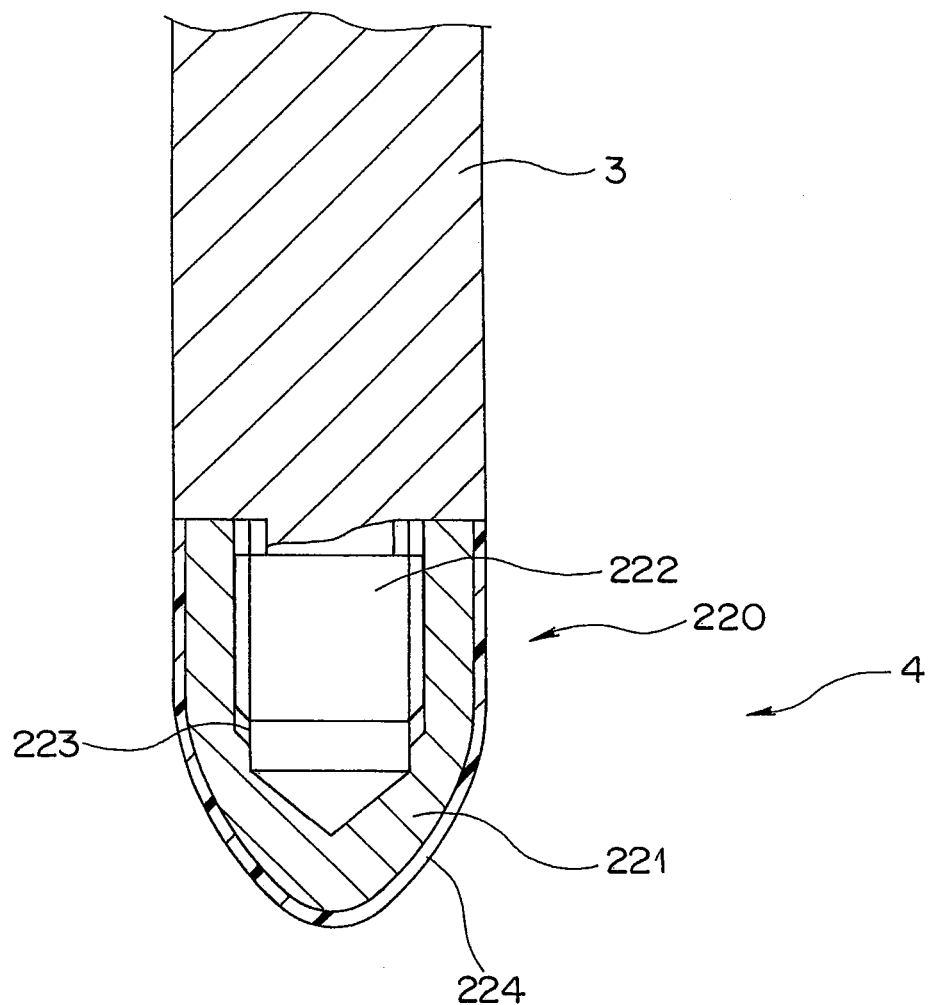
FIG. 21 is a longitudinal sectional view for explaining the construction of a treatment portion of a surgical instrument according to a seventh embodiment.

As shown in FIG. 21, a needle holding member 220 serving as needle holding means comprises a magnet 221 having a substantially conical tapered shape, for example, and an elastic body 224 fixed to the surface of the magnet 221 by fusion. The elastic body 224 is preferably made of, e.g., silicone rubber, fluorine-contained rubber, polyvinyl chloride, or polyurethane.

A threaded hole 223 is formed in a base portion of the magnet 221, and a threaded portion 222 projecting from the distal end of an insert section 3 is screwed into the threaded hole 223. The needle holding member 220 is thereby coupled to the insert section 3.

With such a construction, when the needle 6 is transferred from the needle carrier 10 to the surgical instrument 1, the needle 6 is attracted to the needle holding member 220 by a magnetic force. Thus, the needle 6 can be held by the needle holding member 220 without piercing the needle tip into the elastic body 221. Of course, the needle 6 can also be held by the needle holding member 5 by piercing the needle tip into the elastic body 221.

In addition to substantially the same advantages as those obtained with the first embodiment, this seventh embodiment can provide an advantage that, because even the needle positioned away from the needle holding member can also be attracted to the magnet in the treatment portion 4, the operation for holding again the needle, which has been dropped, for example, in the body cavity, can be easily performed.

An eighth embodiment of the present invention will be described below with reference to FIGS. 22 through 24.

This eighth embodiment differs from the above-described third embodiment in the construction of a part of an operating section and the construction of a treatment portion. The other similar components to those in the third embodiment are denoted by the same numerals and a description of those components is omitted here.

In this embodiment, the link mechanism 40 is used to operate a forceps structure, described later, instead of elastically deforming the needle holding member 60.

Figure 22:
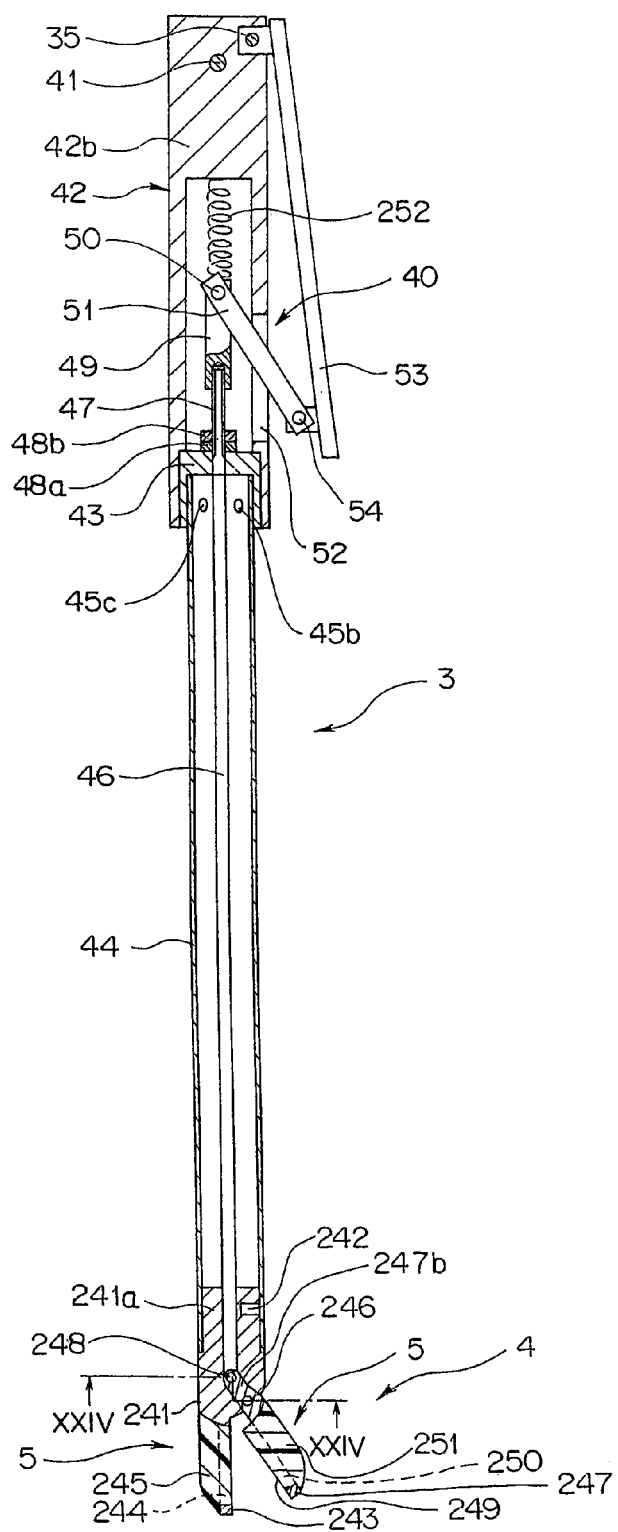
FIG. 22 is a longitudinal sectional view for explaining the construction of a surgical instrument according to an eighth embodiment.

As shown in FIG. 22, in this embodiment, a spring 252 is disposed in a handle portion 42 to bias a joint 49 toward the distal end side.

Figure 23:
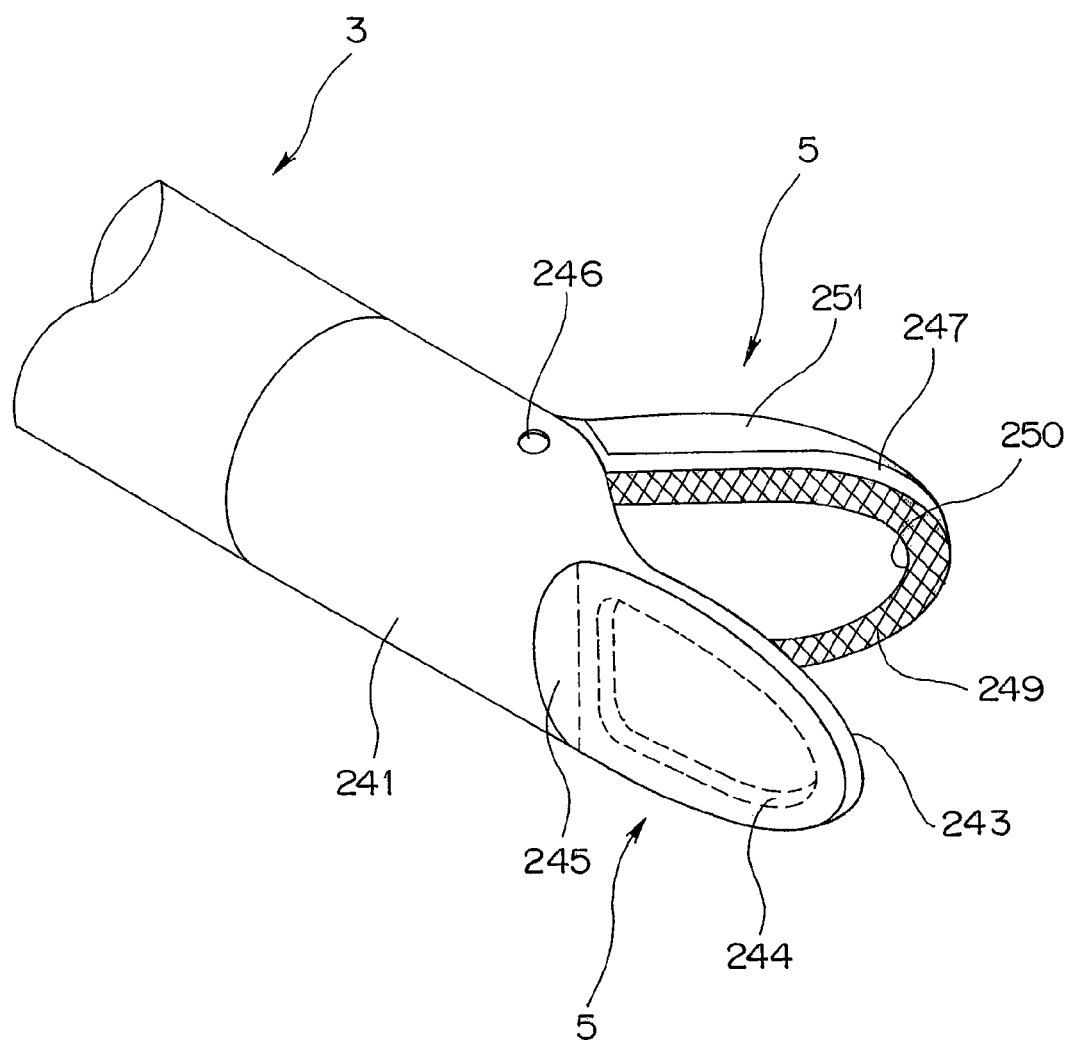
FIG. 23 is a perspective view for explaining the construction of a treatment portion.
Figure 24:
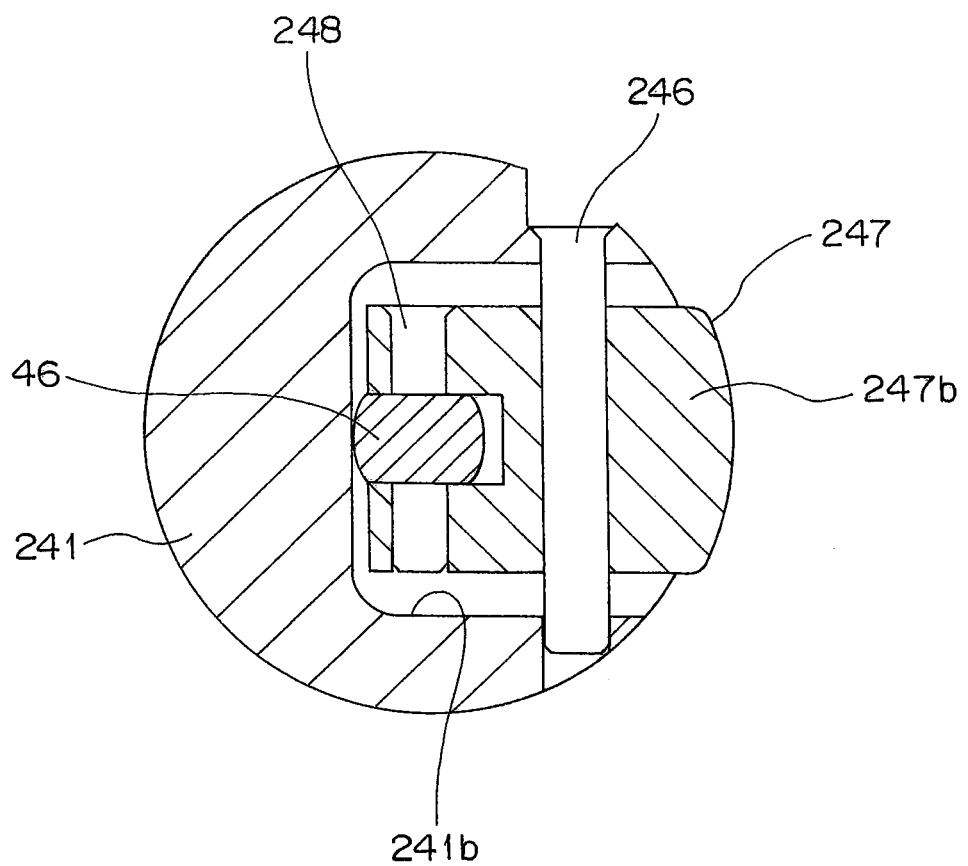
FIG. 24 is a sectional view taken along the line XXIV-XXIV in FIG. 22.

Also, as shown in FIGS. 22 through 24, a fixed pinching piece 241 is coupled to the distal end of an insert section 3. More specifically, the fixed pinching piece 241 has a substantially cylindrical base portion 241a. The base portion 241a is fitted into an outer sleeve 44 of the insert section 3 and is fixed by a screw 242 to be coupled to the insert section 3. A distal end portion of a rod 46 penetrating through the outer sleeve 44 is inserted into the center of the base portion 241a coupled to the insert section 3 such that the rod 46 is able to advance and retract in the longitudinal axial direction.

A pinching surface portion 243 for pinching a needle, etc. is integrally formed at the distal end side of the base portion 241a. The pinching surface portion 243 is made of a substantially ring-shaped member having a through hole 244 formed in its central area. The pinching surface portion 243 is disposed to extend along a plane substantially in match with a plane containing a longitudinal axis of the rod 46 and an axis of a pin 50. The pinching surface portion 243 includes an elastic body 245 constituting a needle holding member 5, which is filled so as to span from the backside of the pinching surface portion 243 to the through hole 244.

At the distal end side of the fixed pinching piece 241, a recess 241b is formed near a joint between the base portion 241a and the pinching surface portion 243. A base portion 247b of a movable pinching piece 247 is disposed in the recess 241b. Also, a pin 246 lying parallel to the pin 50 is supported in the recess 241b. A base portion 247b of the movable pinching piece 247 is pivotably supported by the pin 246. Further, the distal end portion of the rod 46 is rotatably coupled to a proximal end of the base portion 247 through the pin 248 lying parallel to the pin 246.

On the other hand, at the distal end side of the base portion 247b of the movable pinching piece 247, a pinching surface portion 249 is integrally formed in opposed relation to the pinching surface portion 243. The pinching surface portion 249 is made of a substantially ring-shaped member having a through hole 250 formed in its central area. The pinching surface portion 249 includes an elastic body 251 constituting the needle holding member 5, which is filled so as to span from the backside of the pinching surface portion 249 to the through hole 250. With such an arrangement, the forceps structure interlocked with the link mechanism 40 is constituted in the treatment portion 4.

The elastic bodies 245 and 251 are each preferably made of, e.g., silicone rubber, fluorine-contained rubber, polyvinyl chloride, or polyurethane. Also, as shown in FIG. 23, the opposed surfaces of the pinching surface portions 243 and 249 are preferably subjected to a non-slipping process. Preferable examples of the non-slipping process include electrical discharge machining, knurling, and spray of minute diamonds onto a metal plating.

In use of the surgical instrument thus constructed, when the lever 53 is turned down toward the handle portion 42, the joint 49 and the rod 46 are pulled toward the rear end side through the arm 51 against the biasing force of the spring 252. Correspondingly, the movable pinching piece 247 is rotated about the pin 246. As a result, the pinching surface portion 249 is moved toward the pinching surface portion 243 for closing operation.

In addition to substantially the same advantages as those obtained with the first embodiment, this eighth embodiment can provide an advantage that, because of the forceps function being added to the surgical instrument 1, it is possible not only to hold the needle by the needle holding member 5, but also to hold the needle or other tissue, etc. by the opening and closing operation of the pinching surface portion 249. Therefore, the number of times of replacing the surgical instruments during surgery can be reduced.

A ninth embodiment of the present invention will be described below with reference to FIG. 25.

This ninth embodiment differs from the above-described first embodiment in that an opening for sucking water is formed in a treatment portion. The other similar components to those in the first embodiment are denoted by the same numerals and a description of those components is omitted here.

Figure 25:
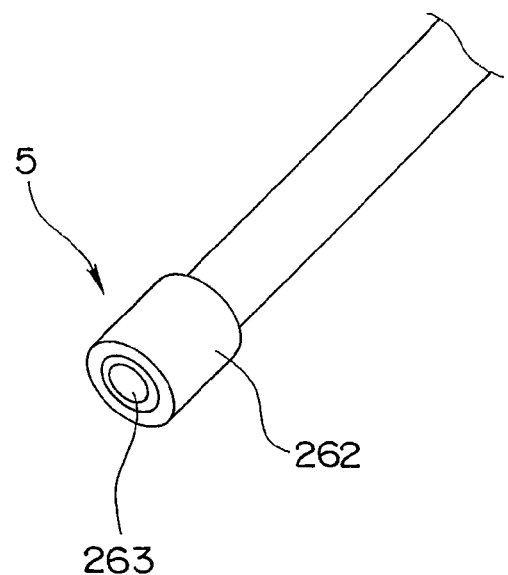
FIG. 25 is a perspective view for explaining the construction of a treatment portion of a surgical instrument according to a ninth embodiment.

In this embodiment, as shown in FIG. 25, a needle holding member 5 includes an elastic body 262 having a substantially cylindrical shape. An opening 263 of a feed line communicating with a suction pump (not shown) is formed at the distal end of the elastic body 262. The elastic body 262 is preferably made of, e.g., silicone rubber, fluorine-contained rubber, polyvinyl chloride, or polyurethane.

With such a construction, the surgical instrument 1 is able to suck liquids, such as body fluids and contaminants near the opening 263, by operation of the feed pump communicating with the feed line.

In addition to substantially the same advantages as those obtained with the first embodiment, this ninth embodiment can provide an advantage that, because of the surgical instrument 1 having the additional water sucking function, the number of the treatment instruments used can be reduced. In the surgery using the endoscope, for example, it is possible to reduce the number of ports to be incised in the patient body for insertion of the treatment instruments, and to realize less-invasive surgery.

A tenth embodiment of the present invention will be described below with reference to FIG. 26.

This tenth embodiment differs from the above-described first embodiment in that a blow opening is formed in a treatment portion. The other similar components to those in the first embodiment are denoted by the same numerals and a description of those components is omitted here.

Figure 26:
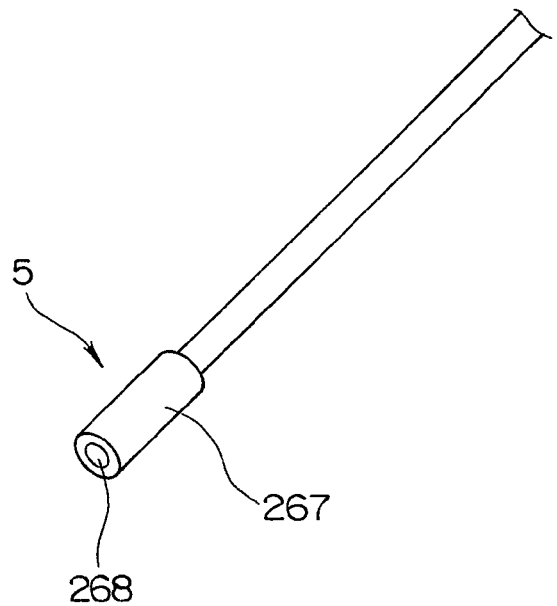
FIG. 26 is a perspective view for explaining the construction of a treatment portion of a surgical instrument according to a tenth embodiment.

In this embodiment, as shown in FIG. 26, a needle holding member 5 includes an elastic body 267 having a substantially cylindrical shape. An opening 268 of a blow passage communicating with a blower (not shown) is formed at the distal end of the elastic body 267. The elastic body 267 is preferably made of, e.g., silicone rubber, fluorine-contained rubber, polyvinyl chloride, or polyurethane.

With such a construction, the surgical instrument 1 is able to remove liquids, such as body fluids and contaminants near the opening 268, by operation of the blower communicating with the blow passage.

In addition to substantially the same advantages as those obtained with the first embodiment, this tenth embodiment can provide an advantage that, because of the surgical instrument 1 having the additional blower function, the number of the treatment instruments used can be reduced. In the surgery using the endoscope, for example, it is possible to reduce the number of ports to be incised in the patient body for insertion of the treatment instruments, and to realize less-invasive surgery.

An eleventh embodiment of the present invention will be described below with reference to FIGS. 27 and 28.

This eleventh embodiment differs from the above-described first embodiment primarily in the construction of a needle holding member. The other similar components to those in the first embodiment are denoted by the same numerals and a description of those components is omitted here.

Figure 27:
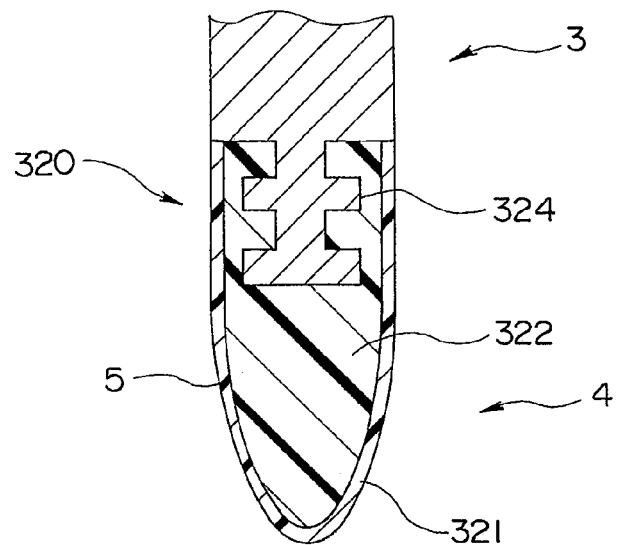
FIG. 27 is a longitudinal sectional view for explaining the construction of a treatment portion of a surgical instrument according to an eleventh embodiment.

As shown in FIG. 27, a stepped projection 324 having a plurality of steps circumferentially formed on its outer periphery is projected from the distal end of an insert section 3. A needle holding member 320 serving as needle holding means, which constitutes a treatment portion 4, is fitted to and supported by the stepped projection 324. Alternatively, the needle holding member 320 may be integrally formed with the stepped projection 324 by, e.g., insert molding.

In this embodiment, the needle holding member 320 is of a two-layered structure having an outer layer 321 and an inner layer 322 each of which is made of an elastic body. The elastic body of the inner layer 322 is more flexible than that of the outer layer 321. Various materials, such as silicone rubber, fluorine-contained rubber, polyvinyl chloride, and polyurethane, can be preferably used for the outer layer 321 and the inner layer 322 of the needle holding member 320.

Figure 28:
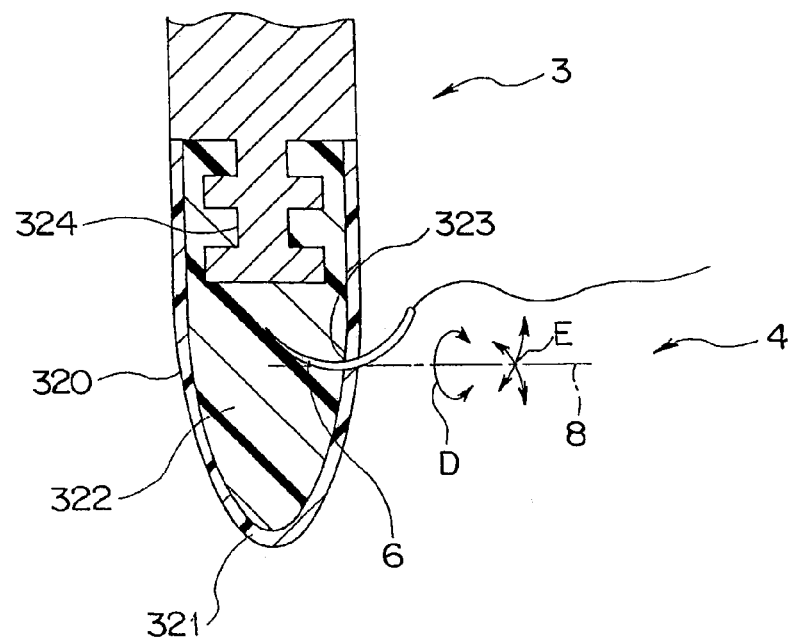
FIG. 28 is a sectional view for explaining the construction and operation of the treatment portion holding the needle.

With such a construction, as shown in FIG. 28, the needle 6 held by the needle holding member 320 is able to not only rotate about an axis 8 of rotation in a direction indicated by an arrow D in the figure, but also to swing in directions indicated by arrows E in the FIGURE about a fulcrum, which is given by a point 323 where the needle is pierced into the outer layer 321, due to a relative difference in hardness between the outer layer 321 and the inner layer 322.

In addition to substantially the same advantages as those obtained with the first embodiment, this eleventh embodiment can provide an advantage that, when the surgeon draws the needle out of a tissue, e.g., a blood vessel, while holding it by the needle holding member 320, the needle 6 is allowed to move three-dimensionally corresponding to a force applied from the tissue. As a result, a tension exerted on the tissue can be more effectively reduced.

A twelfth embodiment of the present invention will be described below with reference to FIGS. 29 through 39.

Figure 29:
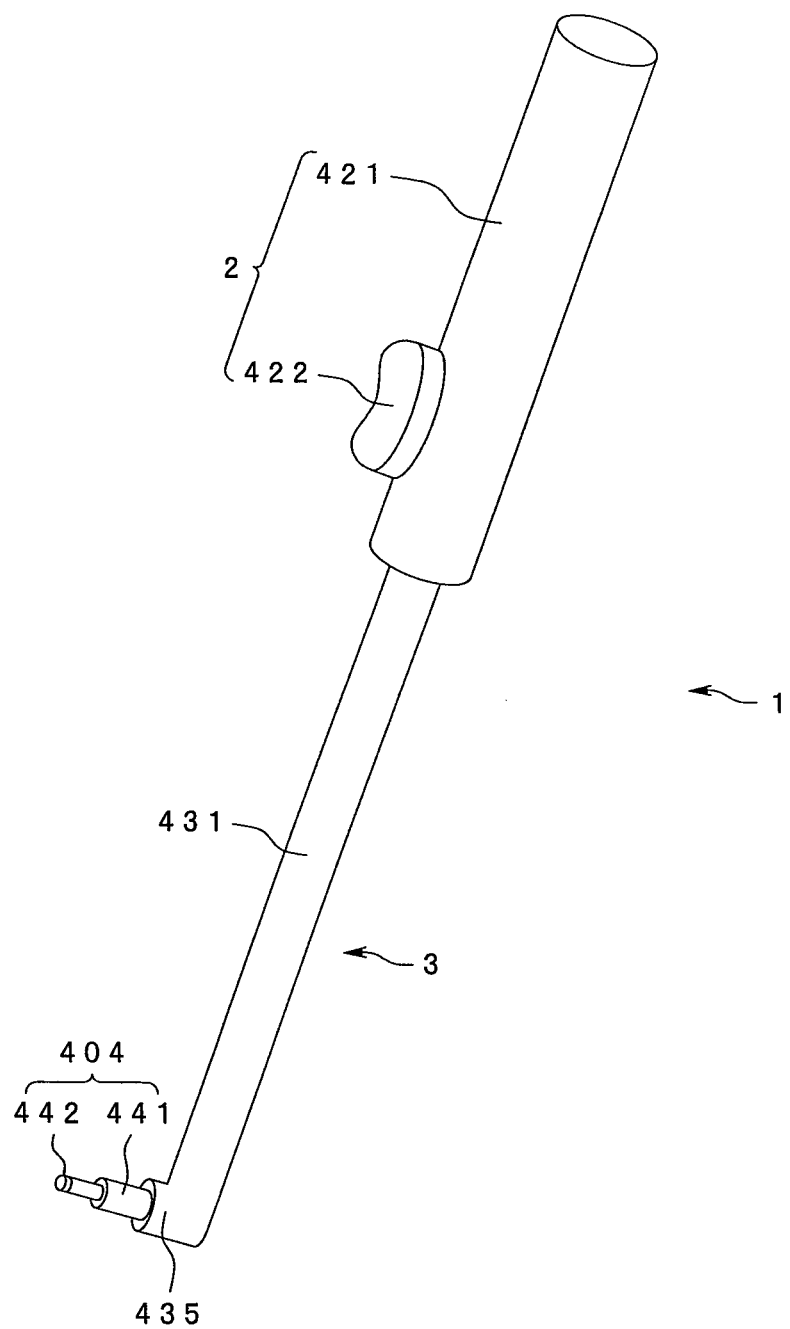
FIG. 29 is a view for explaining the external appearance of a surgical instrument according to a twelfth embodiment in the state where an open/close operating member is placed in an operation start position.

In this embodiment, as shown in FIG. 29, a surgical instrument 1 mainly comprises an operating section 2, an insert section 3, and a clamping portion 404. The operating section 2 also serves as a section grasped by the surgeon. The insert section 3 is extended from one end of the operating section 2. The clamping portion 404 is extended from a bent distal end portion of the insert section 3.

The operating section 2 mainly comprises an operating section body 421 and an operating button 422. The operating button 422 serves as an open/close operating member and is disposed in a distal end portion of the operating section body 421 on its circumferential surface at one side. The clamping portion 404 mainly comprises a clamping portion body 441 and an open/close actuating member 442. The clamping portion body 441 serves as a first clamping member and has a step. The open/close actuating member 442 serves as a second clamping member.

The operating section body 421 is formed of a rigid member, e.g., a resin member. The operating button 422 is formed of a rigid resin member in consideration of a sliding property. The clamping portion body 441 and an open/close actuating member 442 are each formed of a metal member, e.g., stainless steel.

The operating section 2 will be described below with reference to FIGS. 29 and 30.

An operating-section inner space 423 is formed in the operating section body 421 constituting the operating section 2. A button laid hole 424 communicating with the operating-section inner space 423 is formed in a lateral surface of the operating section body 421. A center axis of the button laid hole 424 is substantially perpendicular to the direction of a longitudinal axis of the operating section body 421.

A stepped hole 425 communicating with the operating-section inner space 423 is formed at the center of a distal end wall of the operating section body 421. The stepped hole 425 is constituted by a small diameter hole 425a and a large diameter hole 425b. Respective central axes of the small diameter hole 425a and the large diameter hole 425b are coaxial with each other, and they are substantially aligned with the direction of the longitudinal axis of the operating section body 421.

Though not shown, the operating section body 421 is made up of, for example, a cylindrical member having a proximal end opening and a cover member closing the proximal end opening. The cylindrical member and the cover member are integrally fixed together by fixing means, e.g., bonding or heat sealing.

The operating button 422 is disposed in the button laid hole 424 from the side of the operating-section inner space 423 in such a manner as being capable of freely advancing and retracting. The operating button 422 is advanced and retracted in a direction perpendicular to the direction of the longitudinal axis of the operating section body 421. The operating button 422 comprises a button body 422a, a slip-off check portion 422b, and a projection 422d having a pressing surface 422c. The button body 422a is a solid member and has a cross-section in the elliptic form, for example. The slip-off check portion 422b is projected a predetermined distance from a lateral surface of the button body 422a. The pressing surface 422c is sloped at a predetermined angle. A recess 422e is formed in an end surface of the button body 422a. The recess 422e is provided in consideration of operability when the surgeon holds the operating section 2 by fingers for the operation.

The lateral surface of the button body 422a serves as a sliding surface. The slip-off check portion 422b abuts against an inner peripheral surface 421a of the operating section body 421. With such an arrangement, the operating button 422 is prevented from slipping off to the outside of the operating section body 421. The slope angle of the pressing surface 422c formed in the projection 422d and the amount by which the projection 422d is projected are set in consideration of the amount by which an open/close force transmitting member 432, described later, is moved.

On the other hand, a proximal end portion of an insert section body 431 constituting the insert section 3 is integrally fixed to the large diameter hole 425b of the stepped hole 425 by, e.g., bonding. The insert section body 431 is formed of, e.g., a stainless pipe-like member. Also, a transmitting rod 432 serving as the open/close force transmitting member is inserted through the small diameter hole 425a of the stepped hole 425. The transmitting rod 432 is formed of, e.g., a stainless round rod. The transmitting member 432 is disposed in an inner bore of the insert section body 431 in a slidable manner (i.e., in a freely advancing and retracting manner). Additionally, the inner diameter of the small diameter hole 425a and the inner diameter of the inner bore of the insert section body 431 are substantially equal to each other.

An operating force transmitting block (hereinafter referred to simply as a "transmitting block") 433 is integrally fixed to a proximal end surface of the transmitting rod 432. The transmitting block 433 has a sloped surface 433a. The sloped surface 433a is formed to come into surface contact with the pressing surface 422c of the operating button 422. The outer diameter of the transmitting block 433 is set to be larger than the outer diameter of the transmitting rod 432 by a predetermined size. Between the transmitting block 433 and an inner distal end surface 421b of the operating section body 421, a block biasing coil spring (hereinafter referred to simply as a "coil spring") 434 is disposed in a compressed state. The coil spring 434 has a biasing force acting to move the transmitting block 433 up to a position indicated by broken lines.

The amount by which the projection 422d of the operating section body 421 is projected is set in the state where the slip-off check portion 422b is abutted against the inner peripheral surface 421a. More specifically, that amount is set such that, as indicated by solid lines in the figure, the pressing surface 422c and the sloped surface 433a come into surface contact with each other. Stated another way, the transmitting block 433 is biased by the biasing force of the coil spring 434 so as to move up to a position indicated by the broken lines. However, since the pressing surface 422c is disposed in the state coming into surface contact with the sloped surface 433a of the transmitting block 433, the transmitting block 433 is restricted from further moving toward the proximal end side. The position of the operating button 422 in that state is here called the operation start position.

The relationship between the operating button 422 and the transmitting block 433 will be described below.

A user depresses the operating button 422 located in the operation start position. With movement of the operating button 422 in a direction indicated by an arrow F, the pressing surface 422c is also moved in the direction indicated by the arrow F. At this time, as the pressing surface 422c is moved while sliding over the sloped surface 433a, the transmitting block 433 is gradually moved in a direction indicated by an arrow G against the biasing force of the coil spring 434.

Then, the operating button 422 is further moved in the direction indicated by the arrow F to reach a maximum push-in position where the slip-off check portion 422b abuts against a lateral surface 433b of the transmitting block 433. Upon reaching the maximum push-in position, the movement of the operating button 422 in the direction indicated by the arrow F is stopped and the movement of the transmitting block 433 in the direction indicated by the arrow G is also stopped. In other words, when the slip-off check portion 422b of the operating button 422 abuts against the lateral surface 433b of the transmitting block 433, the transmitting rod 432 is brought into the state where it is maximally stroked toward the distal end side of the insert section body 431.

When, in that maximally stroked state, the user detaches the finger away from the operating button 422 to release it from the depressed state, the transmitting block 433 is moved by the biasing force of the coil spring 434 toward the proximal end side, i.e., in a direction opposed to the direction indicated by the arrow G. This causes the pressing surface 422c to slide over the sloped surface 433a, whereby the operating button 422 is moved in a direction opposed to the direction indicated by the arrow F. As a result, the operating button 422 is returned again to the operation start position.

The insert section 3 and the clamping portion 404 will be described below with reference to FIGS. 29 through 32.

Figure 30:
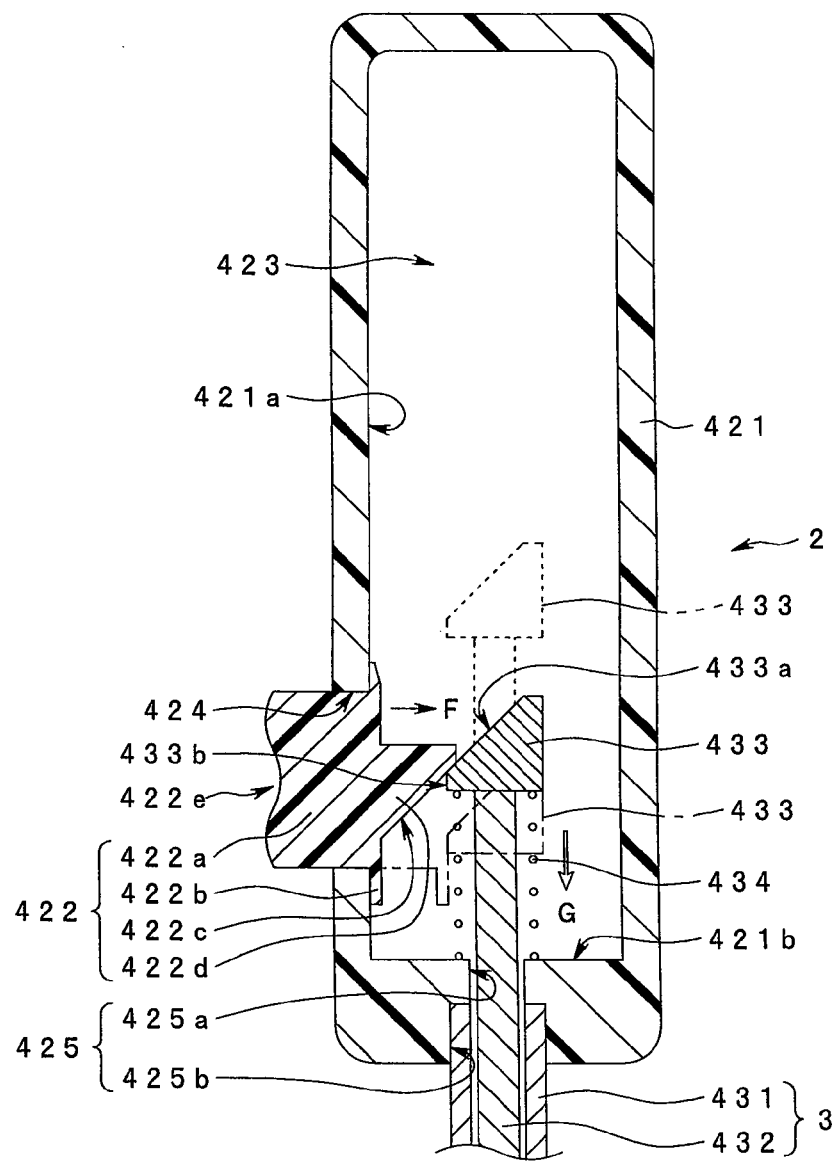
FIG. 30 is a view for explaining the constructions of an operating section and an insert section on its proximal end side in the state where the open/close operating member is placed in the operation start position.
Figure 31:
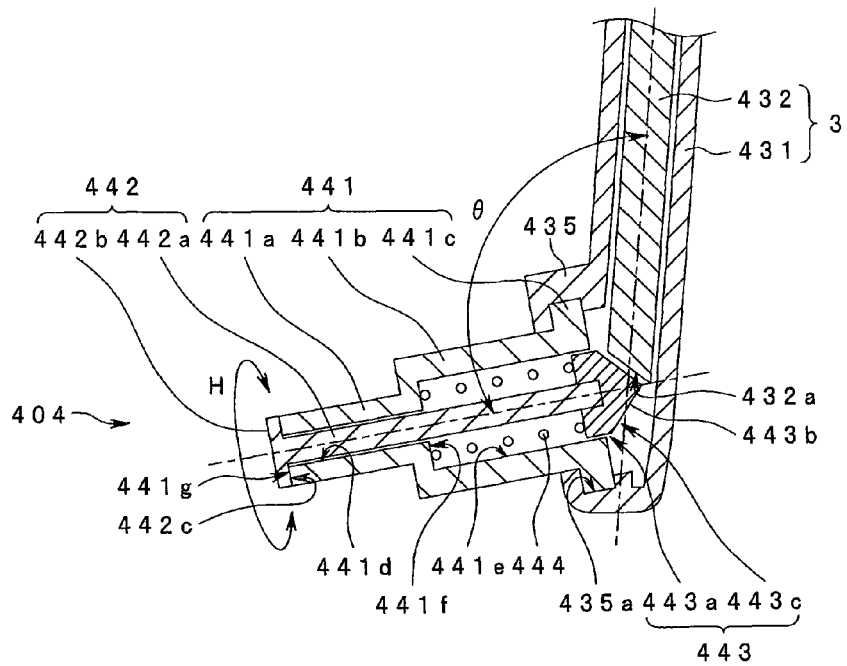
FIG. 31 is a view for explaining the constructions of the insert section on its distal end side and a pinching portion in the state where the open/close operating member is placed in an operation start position.
Figure 32:
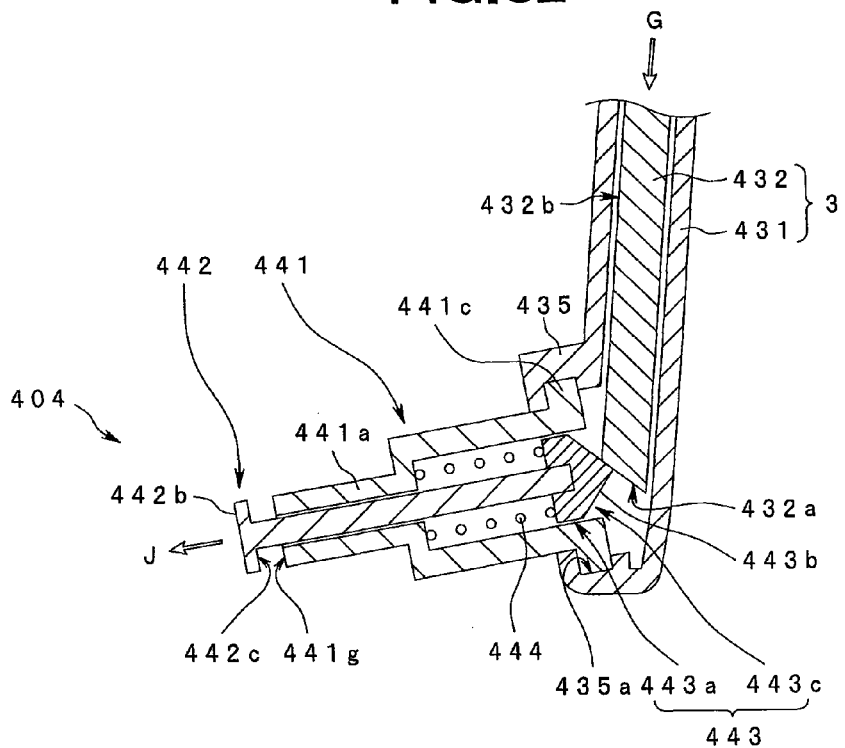
FIG. 32 is a view for explaining the open state of the pinching portion when the open/close operating member is moved to a maximum push position.

As shown in FIGS. 29 through 31, the insert section 3 is constituted by the insert section body 431 in which the transmitting rod 432 is slidably inserted. An insert-section distal end extension 435 having a second axis is provided at a distal end of the insert section body 431. The second axis of the insert-section distal end extension 435 is bent with respect to a first axis, i.e., the longitudinal central axis of the insert section 3, at an angle θ in the range of, e.g., 90° to 140°. A rotation-allowing groove 435a is formed in an inner peripheral surface of the insert-section distal end extension 435 in its distal end region. A projection 441c provided on the clamping portion body 441 and serving as a rotatable holder portion, described later, is rotatably fitted into the rotation-allowing groove 435a.

Further, an open/close force transmitting surface (hereinafter referred to simply as a "transmitting surface") 432a formed to slope at a predetermined angle and serving as a second contact surface is formed at a distal end of the transmitting rod 432. The transmitting surface 432a contacts with a first contact surface, i.e., a receiving surface 443b of a receiving member 443, described later, which is fixed to the open/close actuating member 442.

On the other hand, the clamping portion 404 comprises the clamping portion body 441, the open/close actuating member 442, the receiving member 443, and a clamping bias spring (hereinafter referred to simply as a "clamping spring") 444.

The clamping portion body 441 is formed of a stepped cylindrical member. The clamping portion body 441 is constituted by a small diameter portion 441a, a large diameter portion 441b, and a projection 441c which are continuously formed in this order from the distal end side. A through hole 441d is formed in the small diameter portion 441a. The distal end side of the small diameter portion 441a is constituted as one grasping portion. In the large diameter portion 441b and the projection 441c, a bore 441e is formed at a depth set to a predetermined size from a proximal end surface of the clamping portion body 441. The projection 441c of the clamping portion body 441 is fitted into the rotation-allowing groove 435a, whereby the clamping portion body 441 is rotatably supported such that it is extended from the insert-section distal end extension 435 while being inclined at a predetermined angle.

The open/close actuating member 442 is constituted by a shaft portion 442a and a flange portion 442b. The shaft portion 442a has a predetermined length and is disposed in the through hole 441d in a slidable manner (i.e., in a freely advancing and retracting manner). The flange portion 442b is provided at the distal end of the shaft portion 442a. The flange portion 442b serves as the other grasping portion, and the outer diameter of the flange portion 442b is substantially equal to the outer diameter of the small diameter portion 441a.

Thus, the direction of an axis of rotation of the rotatable clamping portion body 441 is the same as the direction in which the open/close actuating member 442 is opened and closed. In this embodiment, the flange portion 442b has a circular shape. However, the shape of the flange portion 442b is not limited to a circle so long as it is able to clamp a needle. Stated another way, the flange portion 442b may have other suitable shape, such as an elliptic shape or a partly recessed polygonal shape, so long as it has one or more portions radially extending from an axis of the shaft portion 442a.

The receiving member 443 is constituted by a columnar portion 443a and a conical portion 443c having the receiving surface 443b. The columnar portion 443a is slidably disposed in the bore 441e. The receiving surface 443b is formed at a predetermined slope angle such that the transmitting surface 432a contacts with the receiving surface 443b. The receiving member 443 is integrally fixed to the proximal end of the shaft portion 442a by, e.g., bonding.

The clamping spring 444 is a coil spring having a predetermined biasing force. The clamping spring 444 is disposed in a compressed state between a bottom surface 441f of the bore 441e and a distal end surface of the receiving member 443. In such an arrangement, the receiving member 443 is moved by the biasing force of the clamping spring 444 in a direction in which the receiving member 443 is going to be expelled out of an end opening of the bore 441e. At this time, however, a proximal end flat surface 442c of the flange portion 442b abuts against a distal end flat surface 441g of the clamping portion body 441 and comes into close contact with it. Accordingly, the distal end of the columnar portion 443a is prevented from slipping off from the bore 441e and is kept in a state positioned in the bore 441e.

In addition, the projection 441c is rotatably disposed in the rotation-allowing groove 435a. In the sate where the proximal end flat surface 442c and the distal end flat surface 441g are in close contact with each other, therefore, the clamping portion 404 is easily and passively rotatable with respect to the insert-section distal end extension 435, as indicated by an arrow H, upon receiving an external force. The clamping portion 404 comprises the clamping portion body 441, the open/close actuating member 442, the receiving member 443, and the clamping spring 444.

As shown in FIG. 31, the proximal end flat surface 442c of the flange portion 442b is closely contacted with the distal end flat surface 441g of the clamping portion body 441. In that close contact state, the receiving surface 443b and the transmitting surface 432a are in a first position where a slight gap is formed between the receiving surface 443b and the transmitting surface 432a. That positional state is made corresponding to the operation start position of the operating button 422. In other words, the length of the transmitting rod 432 is set such that a slight gap is formed between the transmitting surface 432a and the receiving surface 443b in the state of the operating button 422 being placed in the operation start position.

The relationship among the operating button 422, the transmitting rod 432, and the clamping portion 404 will be described below.

The user depresses the operating button 422 located in the operation start position. With the depression of the operating button 422, as described above, the pressing surface 422c is moved while sliding over the sloped surface 433a. Correspondingly, the transmitting block 433 is gradually moved in the direction indicated by the arrow G against the biasing force of the coil spring 434. Thus, the transmitting block 433 is moved toward the distal end side of the insert section 3.

At this time, the transmitting surface 432a is moved while sliding over the receiving surface 443b. Accordingly, the columnar portion 443a of the receiving member 443 is moved against the biasing force of the clamping spring 444 such that it is gradually pushed into the bore 441e in a direction indicated by an arrow J. As a result, the proximal end flat surface 442c and the distal end flat surface 441g held in the close contact state so far are gradually spaced from each other.

When the operating button 422 is further depressed up to the maximum push-in position, the transmitting surface 432a of the transmitting rod 432 is located on the receiving surface 443b in the state where the transmitting surface 432a is maximally moved toward the insert-section distal end side of the insert section 3. This position corresponds to a second position shown in FIG. 32. At this time, the columnar portion 443a is pushed into the bore 441e by a predetermined amount. As a result, the proximal end flat surface 442c and the distal end flat surface 441g come into a state spaced from each other by a predetermined distance.

In that state, the user detaches the finger away from the operating button 422 to release it from the depressed state. Responsively, the transmitting block 433 is moved by the biasing force of the coil spring 434 toward the proximal end side, i.e., in the direction opposed to the direction indicated by the arrow G. This causes the transmitting rod 432 to be moved in the direction opposed to the direction indicated by the arrow G, whereby the transmitting surface 432a is gradually returned to its original position. At this time, the receiving member 443 is moved by the biasing force of the clamping spring 444 in a direction opposed to the direction indicated by the arrow F. Thus, the operating button 422 is moved in the direction opposed to the direction indicated by the arrow F and is returned again to the operation start position. Also, the receiving member 443 is moved in the direction opposed to the direction indicated by the arrow J, whereby the proximal end flat surface 442c and the distal end flat surface 441g are returned again to the close contact state shown in FIG. 31.

The operation of the thus-constructed surgical instrument 1 will be described below with reference to FIGS. 33 through 36.

Let us now look at an operation of drawing out a suturing needle 453 in the form of a curved needle, which is inserted into a first luminal organ 451 and a second luminal organ 452 with a needle carrier (not shown), by using the surgical instrument 1. The insert section body 431 of the surgical instrument 1 is already introduced into a body cavity through a trocar 456 stuck in a patient body wall 455.

The operation of drawing out the suturing needle 453, which includes a suturing thread 457 attached to the proximal end of the needle, while using an endoscope, is performed as follows.

First, the clamping portion 404 is placed to face a tip of the suturing needle 453 projecting out of the second luminal organ 452 and the second luminal organ 452. Then, the operating button 422 is depressed. With the depression of the operating button 422, the proximal end flat surface 442c of the open/close actuating member 442 and the distal end flat surface 441g of the clamping portion body 441 constituting the clamping portion 404 are spaced from each other. The tip 453a of the suturing needle 453 is placed between the proximal end flat surface 442c and the distal end flat surface 441g.

Figure 33:
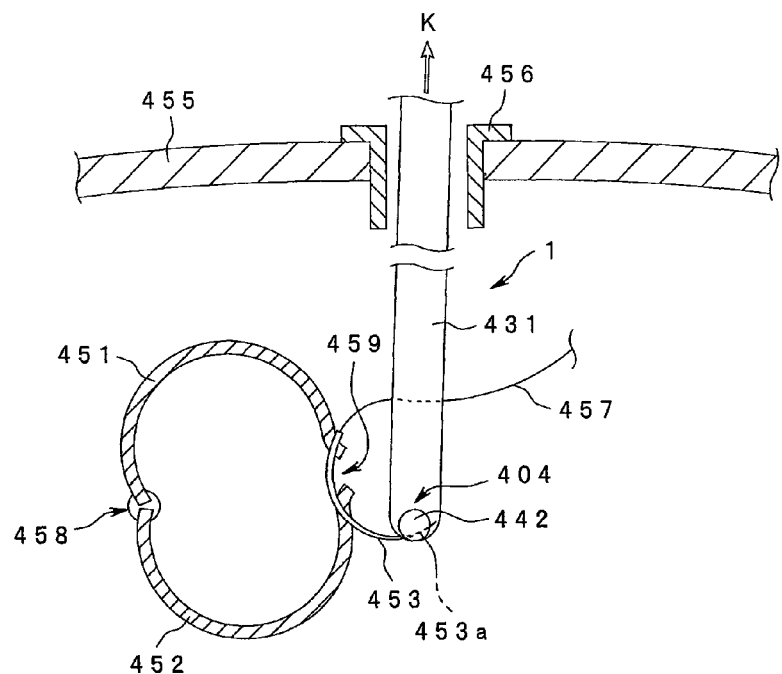
FIG. 33 is an illustration showing the state where a needle tip is grasped by the pinching portion to start the operation of drawing out the needle.

Here, it is confirmed that the tip 453a of the suturing needle 453 is placed between the proximal end flat surface 442c and the distal end flat surface 441g. After the confirmation, the operating button 422 is gradually released from the depressed state. Responsively, the proximal end flat surface 442c and the distal end flat surface 441g are gradually brought into a closed state. Also, the tip 453a of the suturing needle 453 comes into a state grasped by the clamping portion 404 as shown in FIG. 33.

Numeral 458 denotes a portion which has been sutured with the suturing thread 457. Numeral 459 denotes an opening to be sutured, which has been incised by a surgical knife or scissors.

Figure 34:
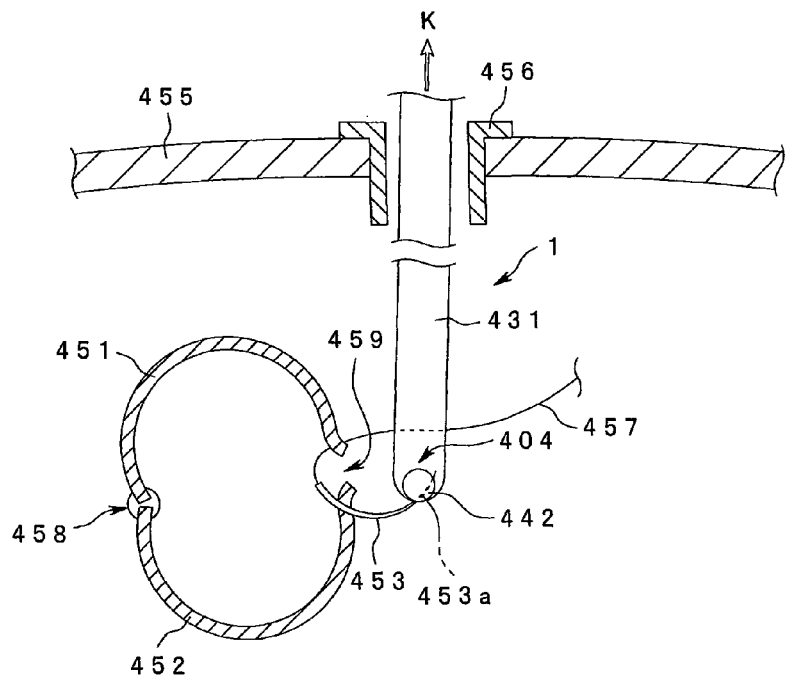
FIG. 34 is an illustration showing the state where the insert section is moved toward a patient body wall such that the proximal end of the suturing needle is drawn out of a first luminal organ.
Figure 35:
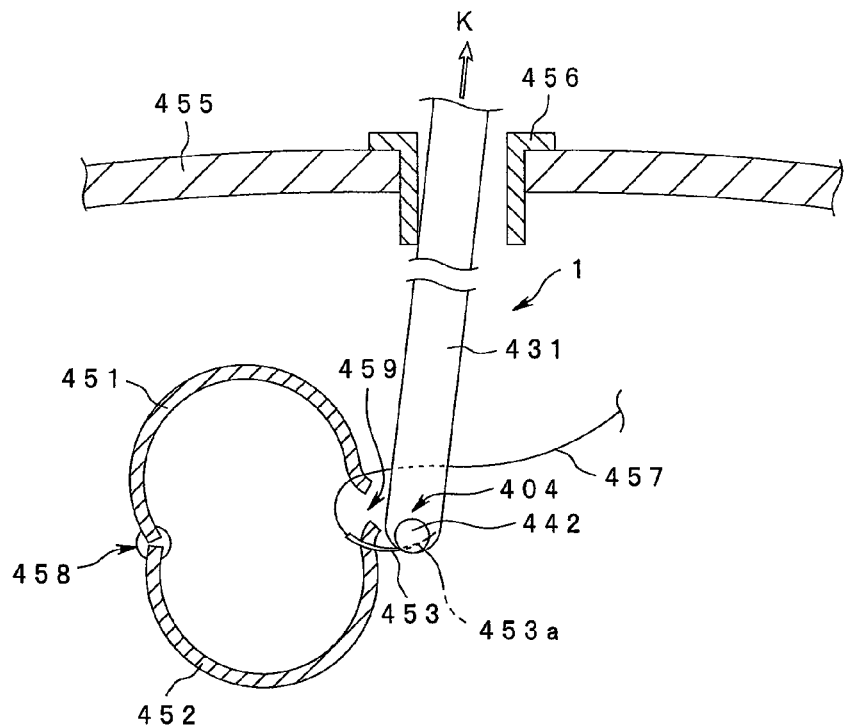
FIG. 35 is an illustration showing the state where the insert section is further moved toward the patient body wall such that the proximal end of the suturing needle reaches a second luminal organ.
Figure 36:
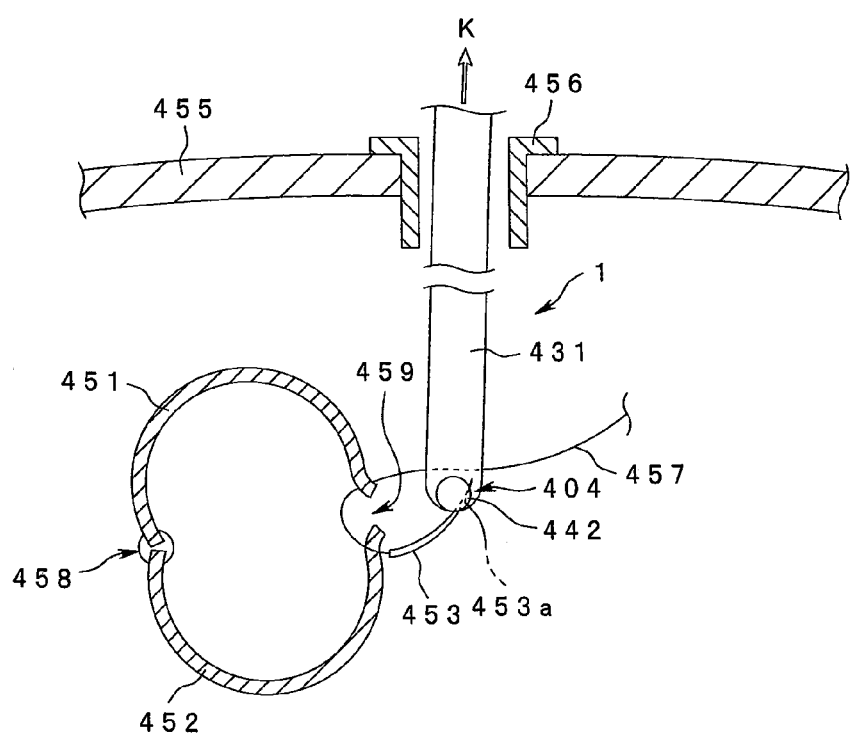
FIG. 36 is an illustration showing the state where the insert section is still further moved toward the patient body wall such that the suturing needle is drawn out of the second luminal organ and a suturing thread is stitched through the first luminal organ and the second luminal organ.

Then, as shown in FIGS. 34, 35 and 36, the surgical instrument 1 is pulled outward to draw the insert section body 431 out of the body cavity as indicated by an arrow K, and at the same time the insert section body 431 is inclined within a limited range. With that inclination, the clamping portion 404 in the state grasping the suturing needle 453 is passively rotated about the second axis relative to the insert-section distal end extension 435. As a result, the suturing needle 453 is drawn out of the first luminal organ 451 and the second luminal organ 452 while gradually changing a path along which the suturing needle 453 is moved.

More specifically, as shown in FIG. 34, when the insert section body 431 is drawn out, an external force is applied to the suturing needle 453, thus generating a rotary motion on the clamping portion 404 with the resulting moment. This causes the clamping portion 404 to be passively rotated about a fulcrum that is given by a point where the suturing needle 453 is pierced into the luminal organ. Therefore, the suturing needle 453 can be drawn out in a natural way without exerting an undue tension on the luminal organs 451 and 452.

Stated another way, after grasping the suturing needle 453 by the clamping portion 404 as shown in FIG. 33, the surgeon pulls the surgical instrument 1 to be drawn out of the body cavity and/or inclines the insert section body 431 within a limited range without performing complicated operations at hand. Correspondingly, the clamping portion 404 is rotated about the fulcrum, i.e., the piercing point of the suturing needle 453, such that the path along which the suturing needle 453 is drawn out is gradually changed.

In this way, the suturing needle 453 is drawn out of the first luminal organ 451 as shown in FIG. 34. Then, as shown in FIG. 35, the suturing needle 453 is moved relative to the second luminal organ 452. Finally, the suturing needle 453 is drawn out of the second luminal organ 452 as shown in FIG. 36, whereby one stitch of suturing the opening 459 to be anastomosed is completed. Subsequently, the surgeon repeats the operations of inserting the suturing needle 453 by using the needle carrier (not shown) and drawing out the suturing needle 453 by using the surgical instrument 1.

In short, the clamping portion body constituting the clamping portion is provided to the insert-section distal end extension in an easily and passively rotatable manner. Also, the clamping portion made up of the clamping portion body, the open/close actuating member, the receiving member and the clamping spring is constituted such that, in the state where the proximal end flat surface of the open/close actuating member and the distal end flat surface of the clamping portion body are in the closed state by the biasing force of the clamping spring, the clamping portion is rotatable upon receiving an external force. With those features, the suturing needle can be quickly drawn out of the luminal organ, etc. by, in the state where the suturing needle is grasped by the clamping portion, pulling up the surgical instrument to be drawn out of the body cavity with no necessity of operating the surgical instrument in a complicated manner.

Thus, the operation of drawing out the needle in the body cavity can be easily performed. Accordingly, the burden imposed on the surgeon can be reduced, and the surgery time can be shortened. Further, manual techniques necessary for the surgery can be learned in a shorter time because of no necessity of operating the surgical instrument in a complicated manner.

Figure 37:
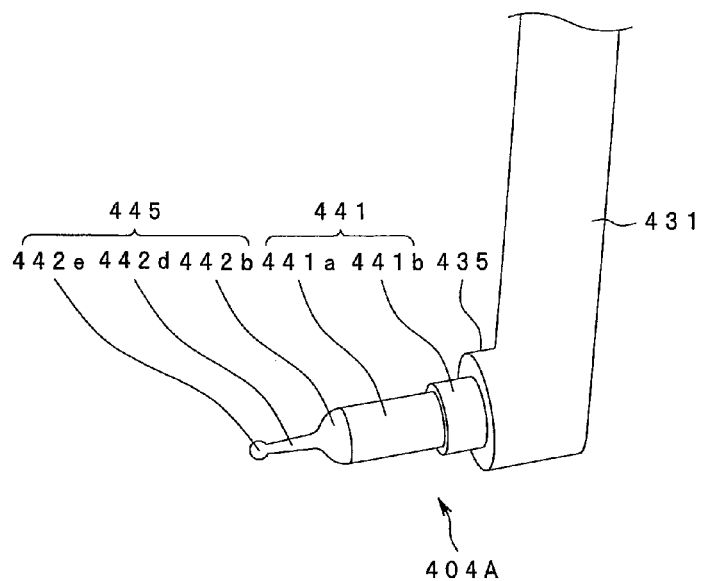
FIG. 37 is an illustration for explaining a pinching portion featured in an open/close actuating member.

The construction of the clamping portion 404 is not limited to the above-described embodiment, and the open/close actuating member 442 disposed in the clamping portion body 441 may be modified to construct a clamping portion 404A, as shown in FIG. 37.

In an open/close actuating member 445 of this modification, a rod 442d having a spherical portion 442e is provided at a distal end surface of the flange portion 442b. The flange portion 442b has the proximal end flat surface 442c coming into close contact with the distal end flat surface 441g of the clamping portion body 441. The other construction is similar to that of the above-described twelfth embodiment. The same components are denoted by the same numerals and a description of those components is omitted here.

The operation of the clamping portion 404A including the open/close actuating member 445 will be described below.

Figure 38:
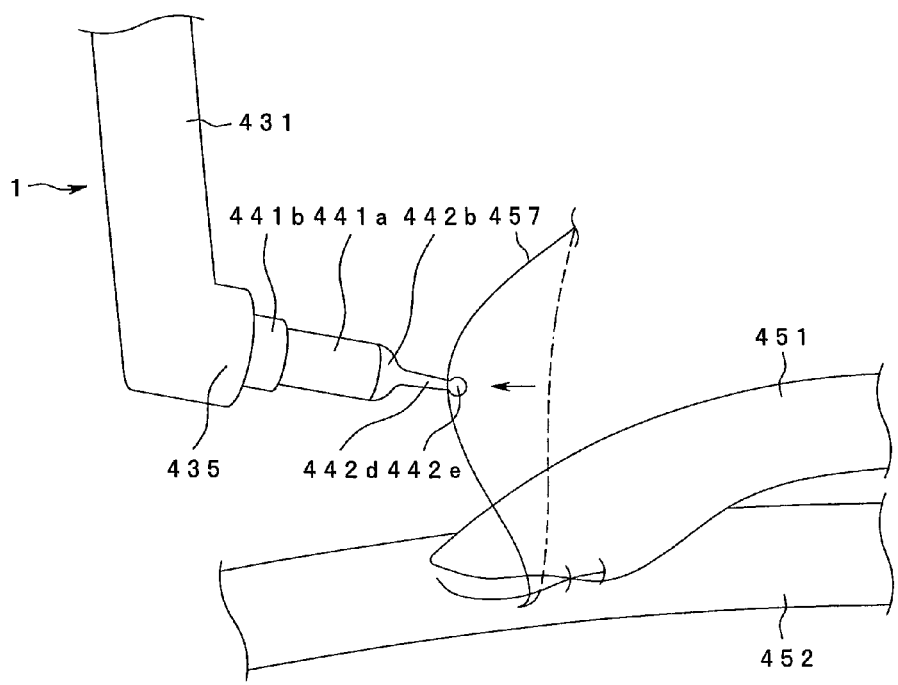
FIG. 38 is an illustration for explaining one action of the pinching portion including the open/close actuating member provided with a rod portion having a spherical end.

First, as shown in FIG. 38, since the rod 442d having the spherical portion 442e is provided at the distal end surface of the flange portion 442b, the operation of moving a thread, i.e., the thread handling, can be performed in the body cavity by catching the suturing thread 457 over the spherical portion 442e without grasping the thread. Also, with the provision of the spherical portion 442e at the distal end of the rod 442d, the luminal organ can be prevented from being damaged in the operation of moving the thread.

Figure 39:
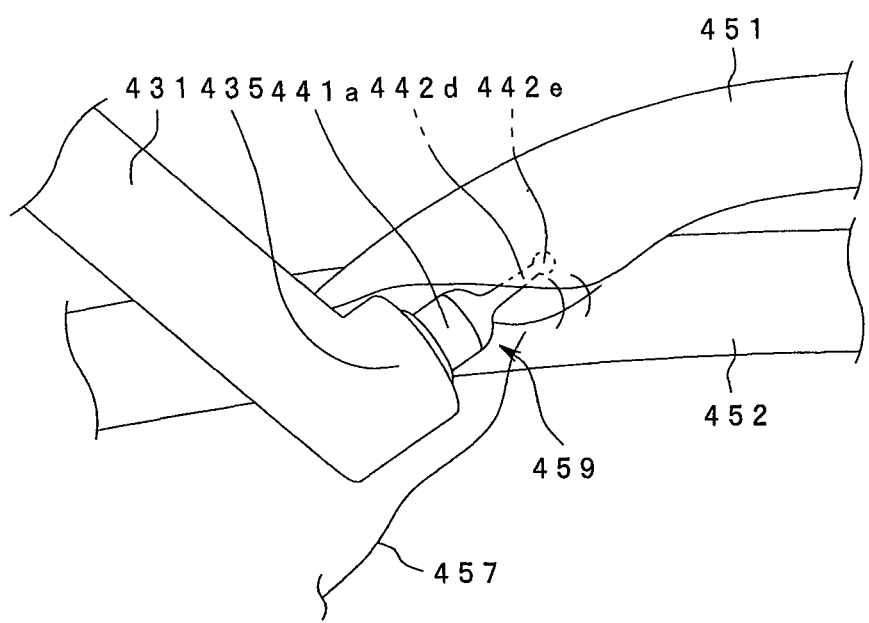
FIG. 39 is an illustration for explaining another action of the pinching portion including the open/close actuating member provided with the rod portion having the spherical end.

Further, as shown in FIG. 39, since the rod 442d having the spherical portion 442e is provided at the distal end surface of the flange portion 442b, the rod 442d can be inserted into the opening 459 to be anastomosed, for example, for lifting the first luminal organ 451 upward. In trying to roll a visual field, therefore, the surgeon can easily roll the visual field without grasping the luminal organ. Also, with the provision of the spherical portion 442e at the distal end of the rod 442d, the luminal organ can be prevented from being damaged in the operation of rolling the visual field.

Thus, because the clamping portion comprises the clamping portion body and the open/close actuating member that includes the rod having the spherical portion, the operation of moving the thread and/or the luminal organ can be easily and safely performed while moving the clamping portion with no need of grasping the target to be treated. As a result, operability of the surgical instrument in the body cavity can be further improved.

It is to be noted that the present invention is not limited only to the above-described embodiments and can be practiced in various forms without departing from the gist of the present invention.

What is claimed is:

1. A surgical instrument configured to draw out an inserted suturing needle, comprising:
   an operating section configured to include an operating section body provided with an operating-section inner space, and an operating button disposed slidably in a button laid hole which is formed to communicate with the operating-section inner space provided in the operating section body;
   an insert section which is a pipe-like member provided with an insert-section distal end extension at a distal end of an insert section body:
   the insert section body being provided to extend from a distal end side of the operating section in a direction perpendicular to a central axis of the button laid hole, and having an inner bore along a first axis in a longitudinal direction, and the insert-section distal end extension having a rotation-allowing groove on an inner peripheral surface of an inner bore provided along a second axis oriented at a predetermined angle with respect to the first axis;

a clamping portion comprising a first clamping member and a second clamping member, a proximal end flat surface of the second clamping member and a distal end flat surface of the first clamping member being movable to be selectively in contact with or apart from each other, the first clamping member including:

the distal end flat surface provided on a distal end side thereof, a rotatable holder portion disposed rotatably in the rotation-allowing groove, and a bore along the second axis and a through hole communicating with the bore and outside the bore, the second clamping member including:

a shaft portion disposed in the first clamping member so as to advance and retract in the through hole and the bore, and so as to rotate around the second axis, a flange portion provided with the proximal end flat surface which is positioned on a distal end side of the shaft portion and opposed to the distal end flat surface, and a receiving member fixed to a proximal end side of the shaft portion and having first contact surface formed to be inclined, a first biasing member disposed at the shaft portion of the second clamping member in the bore of the first clamping member and having a biasing force configured to expel the receiving member out of an opening of the bore and to bring the proximal end flat surface of the second clamping member into contact with the distal end flat surface of the first clamping member;

a transmitting member which is a rod member having a distal end and a proximal end, and has at the a distal end, a second contact surface formed to be brought into surface contact with the first contact surface, a length of the transmitting member being set such that a gap is formed between the second contact surface and the first contact surface in a state where the operating button is not operated, and the transmitting member being disposed movably to advance and retract in the inner bore along the first axis of the insert section body, wherein, when the clamping portion is in a state grasping the suturing needle between the proximal end flat surface of the second clamping member and the distal end flat surface of the first clamping member by the biasing force of the first biasing member, a gap is formed between the second contact surface of the transmitting member disposed movably to advance and retract in the inner bore along the first axis of the insert section body and the first contact surface, to thereby allow the rotatable holder portion of the first clamping member of the clamping portion that grasps the suturing needle to be rotatable relative to the rotation-allowing groove formed on the inner peripheral surface of the inner bore along the second axis, and allow the clamping portion to passively rotate about the second axis, corresponding to an external force applied to the suturing needle.

2. The surgical instrument according to claim 1, further comprising a second biasing member positioned and configured to bias the transmitting member in a direction away from the first contact surface.

3. The surgical instrument according to claim 1, wherein the second axis is inclined at an angle in the range of 90 to 140 degrees relative to the first axis.

4. The surgical instrument according to claim 1, wherein the transmitting member moves between a first position where the clamping portion is in a closed state with a gap being formed between the second contact surface and the first contact surface, and a second position where the proximal end flat surface is apart from the distal end flat surface in the clamping portion by a predetermined distance after the second contact surface is moved slidingly on the first contact surface to push the receiving member to be moved.

\* \* \* \* \*